US010233163B2

(12) United States Patent
Mollenkopf et al.

(10) Patent No.: US 10,233,163 B2
(45) Date of Patent: *Mar. 19, 2019

(54) ACESULFAME POTASSIUM COMPOSITIONS AND PROCESSES FOR PRODUCING SAME

(71) Applicant: Celanese International Corporation, Irving, TX (US)

(72) Inventors: Christoph Mollenkopf, Frankfurt am Main (DE); Peter Groer, Babenhausen (DE); Arvind Yadav, Hessen (IN)

(73) Assignee: Celanese International Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/014,431

(22) Filed: Jun. 21, 2018

(65) Prior Publication Data

US 2018/0297967 A1    Oct. 18, 2018

Related U.S. Application Data

(63) Continuation of application No. 15/704,386, filed on Sep. 14, 2017, now Pat. No. 10,029,999.

(60) Provisional application No. 62/397,509, filed on Sep. 21, 2016.

(51) Int. Cl.
  C07D 291/06 (2006.01)
  A23L 27/30 (2016.01)

(52) U.S. Cl.
  CPC .......... C07D 291/06 (2013.01); A23L 27/30 (2016.08); *A23V 2002/00* (2013.01)

(58) Field of Classification Search
  CPC .............................. C07D 209/06; A23L 27/30
  USPC ........................................................ 544/200
  See application file for complete search history.

(56) References Cited

U.S. PATENT DOCUMENTS

| | | | |
|---|---|---|---|
| 4,563,521 A | 1/1986 | Clauss et al. | |
| 4,607,100 A | 8/1986 | Clauss et al. | |
| 4,638,063 A | 1/1987 | Clauss et al. | |
| 4,695,629 A | 9/1987 | Clauss et al. | |
| 4,804,755 A | 2/1989 | Reuschling et al. | |
| 4,806,639 A | 2/1989 | Reuschling et al. | |
| 4,876,341 A | 10/1989 | Schütz et al. | |
| 5,011,982 A | 4/1991 | Clauss et al. | |
| 5,084,180 A | 1/1992 | Boateng | |
| 5,103,046 A | 4/1992 | Clauss et al. | |
| 5,334,397 A | 8/1994 | Ream et al. | |
| 5,744,010 A | 4/1998 | Roscher et al. | |
| 5,808,159 A | 9/1998 | Giebeler | |
| 7,408,059 B2 | 8/2008 | Kobayashi et al. | |
| 7,977,514 B2 | 7/2011 | Peters et al. | |
| 8,182,756 B2 | 5/2012 | Liu et al. | |
| 8,303,921 B2 | 11/2012 | Brietzke et al. | |
| 8,309,048 B2 | 11/2012 | Brietzke et al. | |
| 8,496,905 B2 | 7/2013 | Brietzke et al. | |
| 8,658,830 B2 | 2/2014 | Brietzke et al. | |
| 9,024,016 B2 | 5/2015 | Bayer et al. | |
| 10,029,999 B2* | 7/2018 | Mollenkopf | A23L 27/30 |
| 2003/0065172 A1 | 4/2003 | Tian et al. | |
| 2003/0065218 A1 | 4/2003 | Mollenkopf | |
| 2008/0076919 A1 | 3/2008 | Liu et al. | |
| 2009/0318685 A1 | 12/2009 | Saito et al. | |
| 2009/0318686 A1 | 12/2009 | Saito et al. | |
| 2010/0274057 A1 | 10/2010 | Peters et al. | |
| 2011/0256045 A1 | 10/2011 | Brietzke et al. | |
| 2011/0256046 A1 | 10/2011 | Brietzke et al. | |
| 2013/0062192 A1 | 3/2013 | Brietzke et al. | |
| 2013/0331565 A1 | 12/2013 | Bayer et al. | |
| 2018/0079733 A1 | 3/2018 | Mollenkopf et al. | |
| 2018/0079735 A1 | 3/2018 | Mollenkopf et al. | |
| 2018/0079736 A1 | 3/2018 | Mollenkopf et al. | |

FOREIGN PATENT DOCUMENTS

| | | |
|---|---|---|
| CA | 1273923 | 9/2009 |
| CN | 85104277 | 6/1985 |
| CN | 85104277 A | 12/1986 |
| CN | 1883790 | 12/2006 |
| CN | 200949088 | 9/2007 |
| CN | 101124981 | 2/2008 |

(Continued)

OTHER PUBLICATIONS

ASTM E 313-05, Standard Practice for Calculating Yellowness and Whiteness Indices from Instrumentally Measured Color Coordinates, Oct. 1, 2005, 6 pages.
Boehshar et al., 5-Chloroacesulfame K—a characteristic indicator for application of the "sulfur trioxide" process in the manufacture of acesulfame K, Research Disclosure, 2003, 477036.
Mayer et al., Acesulfame-K, Food Science and Technology, Jun. 28, 1991.
International Search Report received in the corresponding International PCT Patent application No. PCT/US2007/051512, dated Nov. 9, 2017.
Linkies et al., Synthesis, 1990, 5, 405-406.

(Continued)

*Primary Examiner* — Kahsay Habte
(74) *Attorney, Agent, or Firm* — Dority & Manning, P.A.

(57) ABSTRACT

Compositions and processes for producing high purity acesulfame potassium are described. One process comprises the steps of providing a crude acesulfame potassium composition comprising acesulfame potassium and acetoacetamide, concentrating the crude acesulfame potassium composition to form a water stream and an intermediate acesulfame potassium composition comprising acesulfame potassium and less than 33 wppm acetoacetamide, and separating the intermediate acesulfame potassium composition to form the finished acesulfame potassium composition comprising acesulfame potassium and less than 33 wppm acetoacetamide. The concentrating step is conducted at a temperature below 90° C. and the separating step is conducted at a temperature at or below 35° C.

37 Claims, 2 Drawing Sheets

(56) References Cited

FOREIGN PATENT DOCUMENTS

| | | |
|---|---|---|
| CN | 101124981 A | 2/2008 |
| CN | 101148300 | 3/2008 |
| CN | 101157666 | 4/2008 |
| CN | 101787001 | 7/2010 |
| CN | 101913898 | 12/2010 |
| CN | 201921689 | 8/2011 |
| CN | 102225333 | 10/2011 |
| CN | 102359926 | 2/2012 |
| CN | 102380226 | 3/2012 |
| CN | 102380266 A | 3/2012 |
| CN | 202221403 U | 5/2012 |
| CN | 102866042 | 1/2013 |
| CN | 103018368 | 4/2013 |
| CN | 103130743 | 6/2013 |
| CN | 10331294 | 10/2013 |
| CN | 103570592 | 2/2014 |
| CN | 103570592 A | 2/2014 |
| CN | 103588728 | 2/2014 |
| CN | 103588728 A | 2/2014 |
| CN | 103613566 | 3/2014 |
| CN | 103613566 A | 3/2014 |
| CN | 103960558 | 8/2014 |
| CN | 104193625 | 12/2014 |
| CN | 104209052 | 12/2014 |
| CN | 104225956 | 12/2014 |
| CN | 104292181 | 1/2015 |
| CN | 104292181 A | 1/2015 |
| CN | 204320227 | 5/2015 |
| CN | 105085160 A | 11/2015 |
| CN | 105111166 A | 12/2015 |
| CN | 105152446 | 12/2015 |
| CN | 105198778 | 12/2015 |
| CN | 106262665 | 1/2017 |
| CN | 106267879 | 1/2017 |
| CN | 106346138 | 1/2017 |
| CN | 106349009 | 1/2017 |
| CN | 106349190 | 1/2017 |
| CN | 106349191 | 1/2017 |
| CN | 106349300 | 1/2017 |
| CN | 106365952 | 2/2017 |
| CN | 106496159 A | 3/2017 |
| CN | 206001191 | 3/2017 |
| CN | 206001201 | 3/2017 |
| CN | 206001439 | 3/2017 |
| CN | 206121215 | 4/2017 |
| DE | 1249262 | 10/1966 |
| DE | 1268141 | 5/1968 |
| DE | 3522470 | 1/1987 |
| DE | 3531357 | 3/1987 |
| DE | 3545196 | 6/1987 |
| EP | 0155634 | 9/1985 |
| EP | 0159516 | 10/1985 |
| EP | 0215347 | 3/1987 |
| EP | 0217024 | 4/1987 |
| EP | 0218076 | 4/1987 |
| JP | 54032406 | 3/1979 |
| JP | S 5432406 A | 3/1979 |
| WO | WO93/19055 | 9/1993 |
| WO | WO 2011/133468 A1 | 10/2011 |
| WO | WO2013/182651 | 12/2013 |

OTHER PUBLICATIONS

"Commission Direction 95/31/EC of Jul. 5, 1995 laying down specific criteria of purity concerning sweeteners for use in foodstuffs," Official Journal of the European Communities, Jul. 28, 1995, 19 pages.

"Commission Direction 2008/60/EC of Jun. 17, 2008 laying down specific purity criteria concerning sweeteners for use in foodstuffs," Official Journal of the European Union, Jun. 18, 2008, 40 pages.

"Regulations—Commission Regulation (EU) No. 231/2012 of Mar. 9, 2012 laying down specifications for food additives listed in Annexes II and II to Regulation (EC) No. 1333/2008 of the European Parliament and of the Council," Official Journal of the European Union, Mar. 22, 2012, 295 pages.

Opinion—"Re-evaluation of acesulfame K with reference to the previous SCF opinion of 1991," European Commission , Health & Consumer Protection Directorate-General, Directorate B—Scientific Health Opinions, Unit B3—Management of Scientific Committees II, Scientific Committee on Food, Mar. 13, 2000, 8 pages.

Product Information on "Acesulfame Potassium," 2001, 57th JECFA (joint FAO/WHO Expert Committee on Food Additives), FNP 52 Add 9, 2 pages.

Suenaga, "Ethylene-amine salt recovery—by converting the hydrochloride into the sulphate, and reacting with ammonia in aq. Solvent to ppte. Ammonium sulphate", WPI/Thompson, 1979, No. 16, XP 002598345 (See JP54032406).

Sunnett Brochure, "Acesulfame Potassium", Celanese, Apr. 2014.

Xiangsheng et al., "Synthesis of Acesulfame Potassium", Fine Chemicals, vol. 13, 1996, 1-15.

Information Disclosure Statement submitted Oct. 27, 2017, 2 pages.

Boehshar, Manfred & Burgard, Andreas. (2003). 5-Chloroacesulfame K—a characteristic indicator for application of the "sulfur trioxide" process in the manufacture of acesulfame K. Research Disclosure, 477036.

D. Mayer, et al., Acesulfame-K (Food Science and Technology), 1991, Intro., Chapters 15, 16, and 18, 56 pages.

\* cited by examiner

ACESULFAME POTASSIUM COMPOSITIONS AND PROCESSES FOR PRODUCING SAME

CROSS-REFERENCE TO RELATED APPLICATIONS

This patent application is a continuation of U.S. application Ser. No. 15/704,386 having a filing date of Sep. 14, 2017, which claims priority to U.S. Provisional Patent Application No. 62/397,509, filed Sep. 21, 2016, the disclosures of which are incorporated herein by reference in their entirety.

FIELD OF INVENTION

The present invention relates generally to acesulfame potassium and to processes for producing acesulfame potassium. More specifically, the present invention relates to processes for producing high purity acesulfame potassium.

BACKGROUND OF THE INVENTION

Acesulfame potassium has an intense, sweet taste and has been used in many food-related applications as a sweetener. In conventional acesulfame potassium production processes, sulfamic acid and an amine, e.g., triethylamine, are reacted to form an amidosulfamic acid salt, such as a trialkyl ammonium amidosulfamic acid salt. The amidosulfamic acid salt is then reacted with diketene to form an acetoacetamide salt. The acetoacetamide salt may be cyclized, hydrolyzed, and neutralized to form acesulfame potassium. U.S. Pat. Nos. 5,744,010 and 9,024,016 disclose exemplary acesulfame potassium production processes.

Typically, the acetoacetamide salt intermediate is cyclized by reaction with sulfur trioxide in an inorganic or organic solvent to form a cyclic sulfur trioxide adduct. The solvent routinely utilized in this reaction is an organic solvent such as a halogenated, aliphatic hydrocarbon solvent, for example, dichloromethane. The adduct formed by this reaction is subsequently hydrolyzed and then neutralized with potassium hydroxide to form acesulfame potassium.

Acesulfame potassium product and the intermediate compositions produced by conventional methods contain undesirable impurities, such as acetoacetamide (and acetoacetamide-N-sulfonic acid). Limits for the content of various impurities are often set by governmental regulations or customer guidelines. Removal of many of these impurities using standard purification procedures such as evaporation, crystallization, and/or filtration has proven difficult, resulting in consumer dissatisfaction and the failure to meet standards.

The need exists for improved processes for producing high purity acesulfame potassium compositions in which the formation of impurities such as acetoacetamide during synthesis is reduced or eliminated.

All of the references discussed herein are hereby incorporated by reference.

SUMMARY OF THE INVENTION

The application discloses processes for producing a finished acesulfame potassium composition, the processes comprising the steps of: providing a crude acesulfame potassium composition comprising acesulfame potassium, acetoacetamide and water, concentrating the crude acesulfame potassium composition to form a water stream and an intermediate acesulfame potassium composition comprising acesulfame potassium and less than 33 wppm acetoacetamide (and optionally less than 33 wppm acetoacetamide-N-sulfonic acid), and separating the intermediate acesulfame potassium composition to form the finished acesulfame potassium composition comprising acesulfame potassium and less than 33 wppm acetoacetamide. The concentrating step is conducted at a temperature below 90° C., and the separating step is conducted at a temperature at or below 35° C. The weight percentage of acetoacetamide in the finished acesulfame potassium composition may be less than the weight percentage of acetoacetamide in the crude acesulfame potassium composition. The intermediate acesulfame potassium composition may comprise less than 33 wppm acetoacetamide-N-sulfonic acid. The providing of the crude acesulfame composition may comprise the steps of reacting sulfamic acid and an amine to form an amidosulfamic acid salt, reacting the amidosulfamic acid salt and acetoacetylating agent to form an acetoacetamide salt, reacting the acetoacetamide salt with cyclizing agent in the cyclizing agent composition to form the cyclic sulfur trioxide adduct, hydrolyzing the cyclic sulfur trioxide adduct to form an acesulfame-H composition comprising acesulfame-H, and neutralizing the acesulfame-H in the acesulfame-H composition to form the crude acesulfame potassium composition comprising acesulfame potassium and acetoacetamide. The concentrating step may comprise evaporating the crude acesulfame potassium composition to form the water stream and the intermediate acesulfame potassium composition comprising acesulfame potassium and less than 75 wt % water, and the evaporation residence time may be less than 180 minutes. The separating may comprise crystallizing the intermediate acesulfame potassium composition to form acesulfame potassium crystals and filtering the acesulfame potassium crystals to form the finished acesulfame potassium composition. Preferably, the concentrating comprises evaporating the crude acesulfame potassium composition to form a water stream and an intermediate acesulfame potassium composition comprising acesulfame potassium and less than 50 wt % water, and the separating comprises crystallizing the intermediate acesulfame potassium composition to form a crystal-containing stream comprising acesulfame potassium crystals, and filtering the crystal-containing stream to form the finished acesulfame potassium composition. The filtering may be conducted at a temperature at or below 35° C. and/or the crystallizing may be conducted at a temperature at or below 35° C. and/or may comprise at least two filtration operations. In some cases, the evaporating may be conducted at a temperature below 85° C. and the intermediate acesulfame potassium composition may comprise from 1 wppb to 33 wppm acetoacetamide (and optionally less than 33 wppm acetoacetamide-N-sulfonic acid) and the finished acesulfame potassium composition may comprise less than 33 wppm acetoacetamide. In one embodiment, the evaporating may be conducted at a temperature below 60° C. and the evaporator residence time is less than 50 minutes and the intermediate acesulfame potassium composition may comprise from 10 wppb to 25 wppm acetoacetamide (and optionally less than 30 wppm acetoacetamide-N-sulfonic acid) and the finished acesulfame potassium composition may comprise from 10 wppb to 15 wppm acetoacetamide. In one embodiment, the evaporating may be conducted at a temperature below 46° C., the evaporator residence time may be less than 30 minutes, the crystallizing may be conducted at a temperature below 35° C., the intermediate acesulfame potassium composition may comprise from 10 wppb to 12 wppm acetoacetamide (and optionally less than 20 wppm acetoacetamide-N-sulfonic acid), and the finished acesulfame potassium composition may comprise from 10 wppb to 7 wppm acetoacetamide. In some cases, the evaporating is conducted at a temperature ranging from 20° C. to 55° C.; the evaporator residence time ranges from 1 minute to 300 minutes; the separating is conducted at a temperature ranging from −10° C. to 15° C.; the separating operation residence time ranges from 1 to 180 minutes; the crude acesulfame potassium composition comprises from 500 wppm to 2375 wppm acetoacetamide; the intermediate acesulfame potassium composition comprises 10 wppb to 20 wppm acetoacetamide and 10 wppb to 20 wppm acetoacetamide-N-sulfonic acid; and the finished acesulfame potassium composition comprises from 10 wppb to 10 wppm acetoacetamide, and from 1 wppb to 20 wppm acetoacetamide-N-sulfonic acid. The crystallizing may be conducted at a pH below 10. The crude acesulfame composition may further comprise solvent and wherein the process may further comprise removing solvent from the crude acesulfame potassium composition prior to the evaporation. The processes may comprise the step of separating from the acesulfame-H composition a transition phase comprising at least 2 wt % acetoacetamide to form a purified acesulfame-H composition, and the neutralizing may comprise neutralizing the acesulfame-H in the purified acesulfame-H composition to form the crude acesulfame potassium composition comprising acesulfame potassium and acetoacetamide. In one embodiment, the process comprises the steps of reacting sulfamic acid and triethylamine to form an amidosulfamic acid salt, reacting the amidosulfamic acid salt and diketene to form acetoacetamide salt, contacting dichloromethane and a sulfur trioxide to form a cyclizing agent composition, reacting the acetoacetamide salt with sulfur trioxide in the cyclizing agent composition to form a cyclic sulfur trioxide adduct, hydrolyzing the cyclic sulfur trioxide adduct to form an acesulfame-H composition, neutralizing the acesulfame-H to form the crude acesulfame potassium composition comprising acesulfame potassium and acetoacetamide, evaporating the crude acesulfame potassium composition to form a water stream and an intermediate acesulfame potassium composition comprising acesulfame potassium and less than 75 wt % water, crystallizing the intermediate acesulfame potassium composition to form acesulfame potassium crystals; and filtering the acesulfame potassium crystals to form the finished acesulfame potassium composition comprising acesulfame potassium and less than 10 wppm acetoacetamide. The evaporating may be conducted at a temperature below 50° C., evaporator residence time may be less than 30 minutes filtering may be conducted at a temperature below 35° C., and/or crystallizing may be conducted at a temperature below 35° C. The application also describes crude, intermediate, and finished acesulfame potassium composition produced by the processes described herein. In some cases, the application describes an acesulfame potassium composition comprising acesulfame potassium and less than 33 wppm, preferably less than 10 wppm acetoacetamide and optionally further comprises less than 33 wppm, preferably less than 10 wppm acetoacetamide-N-sulfonic acid. In some cases, the acesulfame potassium composition further comprises 0.001 wppm to 5 wppm organic impurities and/or 0.001 wppm to 5 wppm of at least one heavy metal, e.g., the at least one heavy metal being selected from the group consisting of mercury, lead and mixtures thereof. In some cases, the acesulfame potassium composition further comprises mercury present in an amount of 1 wppb to 20 wppm and/or lead present in an amount of 1 wppb to 25 wppm.

BRIEF DESCRIPTION OF THE DRAWINGS

The invention is described in detail below with reference to the appended drawing.

DETAILED DESCRIPTION OF THE INVENTION

Introduction

Figure 1:
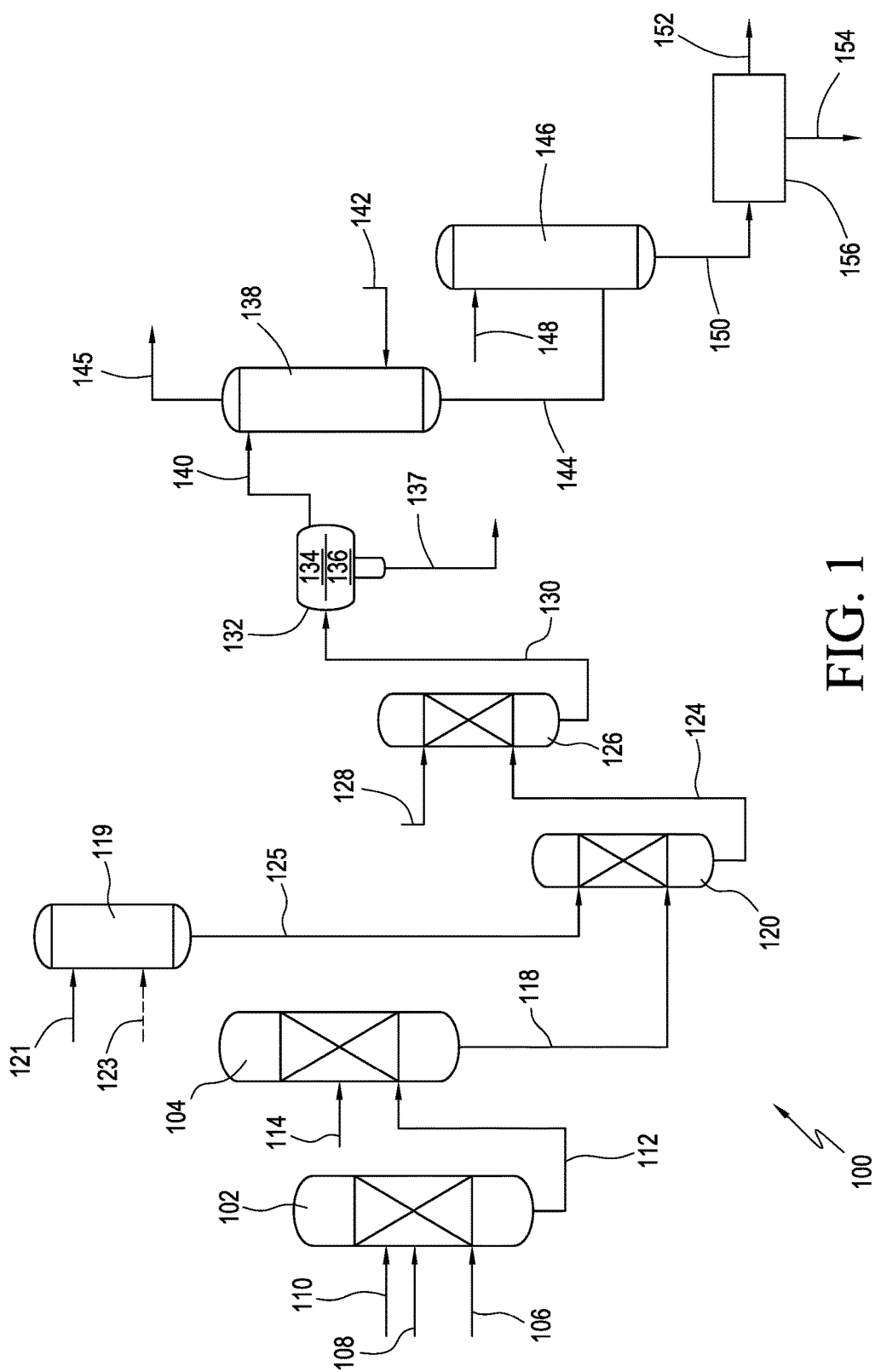
FIG. 1 is a process flow sheet of an acesulfame potassium production process in accordance with one embodiment of the present invention.

Conventional processes for producing acesulfame potassium involve reacting sulfamic acid and an amine in the presence of acetic acid to form an amidosulfamic acid salt. The amidosulfamic acid salt is then reacted with an acetoacetylating agent, e.g., diketene, to form an acetoacetamide salt. The acetoacetamide salt is reacted with a cyclizing agent, e.g., sulfur trioxide, to form a cyclic sulfur trioxide adduct. The cyclic sulfur trioxide adduct is then hydrolyzed and neutralized via conventional means to form a crude acesulfame potassium composition comprising acesulfame potassium. This composition is phase separated into aqueous and organic phases. Most of the acesulfame potassium separates into the aqueous phase. As used herein, the term "crude acesulfame potassium composition" refers to the initial product of the neutralization reaction or to the aqueous phase that is formed from the phase separation step (without any further purification). The crude acesulfame potassium composition comprises at least 5 wt % acesulfame potassium. The crude acesulfame potassium composition may be optionally treated to form an "intermediate acesulfame potassium composition" and/or a "finished acesulfame potassium composition," which are discussed below.

Conventional acesulfame potassium compositions have been shown to comprise several undesirable impurities, among them acetoacetamide and acetoacetamide salts, e.g., acetoacetamide-N-sulfonate triethylammonium salt. Acetoacetamide-N-sulfonic acid and salts thereof may also be present. Content limits for these compounds in the finished acesulfame potassium composition are often determined by industry purity standards and/or by standards established for particular end use products that utilize acesulfame potassium as a sweetener. In some cases, limits for these impurities are determined by governmental regulations. For most applications, high acesulfame potassium purity levels are preferred. Thus, crude acesulfame potassium compositions typically are treated through various treatment operations to reduce the presence of these impurities. A non-limiting list of such treatment operations includes: evaporation, crystallization, and/or filtration.

Without being bound by theory, it has now been discovered that these treatment operations may create stress, e.g., thermal stress, on acesulfame potassium molecules. This thermal stress may also affect acesulfame-H, also known as sweetener acid, which is formed during the hydrolysis step and is a precursor to the acesulfame potassium. This stress on the acesulfame potassium and potentially on the acesulfame-H can result in degradation of these compounds, resulting in the formation of undesirable impurities. In some situations, this stress may cause the acesulfame potassium/acesulfame-H to degrade into its formation reaction reactants, e.g., acetoacetamide and/or salts thereof and/or acetoacetamide-N-sulfonic acid, which can lead to the formation of additional impurities.

It has also now been discovered that the use of specific treatment parameters may advantageously reduce or eliminate stress on the acesulfame potassium (or acesulfame-H) and/or reduce or eliminate product degradation, which in turn reduces or eliminates the formation of additional impurities and ultimately leads to a high-purity end product.

In particular, conducting the treatment (or the individual treatment steps) within certain temperature ranges or limits and/or maintaining treatment residence time within certain time ranges or limits now has been found to surprisingly reduce or eliminate acesulfame potassium (or acesulfame-H) degradation and impurity formation, examples of which include the (re)formation acetoacetamide and salts thereof. Traditionally, the treatment operations, e.g., evaporations, have been conducted at higher temperatures so as to improve process speed and by rapidly removing water. The reduced degradation of acesulfame potassium and acesulfame-H leads directly to the formation of the higher purity crude acesulfame potassium compositions discussed herein, thereby simplifying subsequent treatment operations for forming the intermediate or finished acesulfame potassium compositions. The process also advantageously leads to the formation of intermediate and finished acesulfame potassium compositions having low acetoacetamide-N-sulfamic acid and/or acetoacetamide content.

Additional specific terms that are used herein are now defined.

"Acetoacetamide-N-sulfonic acid" as used herein, refers to the molecule shown below. In some cases, acetoacetamide-N-sulfonic acid may be a degradation product of acesulfame potassium or acesulfame-H. The term "acetoacetamide-N-sulfonic acid," as used herein, also includes salts of acetoacetamide-N-sulfamic acid, e.g., potassium, sodium, and other alkali metal salts.

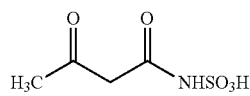

"Acetoacetamide," as used herein, refers to the following molecule:

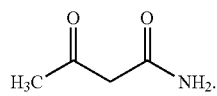

Crude acesulfame compositions may be treated to form intermediate acesulfame potassium compositions and finished acesulfame compositions, and this treatment step may include one or more concentrating or separating operations.

An "intermediate acesulfame potassium composition" refers to a composition resulting from the concentrating of the crude acesulfame potassium composition, e.g., the removal of water from the crude acesulfame potassium composition. The intermediate acesulfame potassium composition comprises at least 10 wt % acesulfame potassium, based on the total weight of the intermediate acesulfame potassium composition, and has an acesulfame potassium weight percentage that is higher than that of the crude acesulfame potassium composition.

A "finished acesulfame potassium composition" refers to a composition (preferably directly) resulting from the separating, e.g., crystallizing and/or filtering, of the intermediate acesulfame potassium composition. The finished acesulfame potassium composition comprises at least 15 wt % acesulfame potassium, based on the total weight percentage of the finished acesulfame potassium composition, and has an acesulfame potassium weight percentage that is higher than that of the intermediate acesulfame potassium composition.

"Residence time," as used herein, refers to the time period that a composition (or stream) to be treated, e.g., a crude acesulfame potassium composition, remains in a particular treatment operation. Residence time begins when the composition to be treated enters the treatment operation, and residence time ends when the resultant compositions (formed via the treatment) exit the treatment operation. As one particular example, residence time for a concentrating operation, e.g., evaporation, refers to the time from when a crude acesulfame potassium composition enters the evaporator until the intermediate acesulfame potassium composition exits the evaporator. As another example, residence time for a separating operation, e.g., crystallization, refers to the time from when a crude acesulfame potassium composition enters the crystallizer until the intermediate acesulfame potassium composition exits the crystallizer.

The treatment of the crude acesulfame potassium composition may entail one or more operations, e.g., a concentrating operation and/or a separating operation. Generally, a concentrating operation is not considered a separating operation. In some embodiments, the concentrating operation(s) and the separating operation(s) make up the overall treatment of the crude acesulfame potassium composition, which results in the finished acesulfame potassium composition. In some cases, the overall concentrating operation may include multiple individual concentrating operations or units and the overall separating operation may include multiple individual separating operations or units.

"Cyclization reaction time," as used herein, refers to the time from the start of the acetoacetamide salt feed to the termination of the acetoacetamide salt feed. In some cases, if indicated, the cyclization reaction time may include additional time past the termination of the acetoacetamide salt feed, e.g., an extra 5 minutes or an extra minute.

"Wppm" and "wppb," as used herein, mean weight parts per million or weight parts per billion, respectively, and are based on the total weight of the entire respective composition, e.g., the total weight of the entire crude acesulfame potassium composition or the entire finished acesulfame potassium composition.

Acesulfame Potassium Formation

Processes for producing high purity acesulfame potassium compositions are described herein. In one embodiment, the process comprises the steps of providing a crude acesulfame potassium composition comprising acesulfame potassium and acetoacetamide (optionally present in an amount ranging from 1 wppb to 50 wppm) and treating the crude acesulfame potassium composition to form a finished acesulfame potassium composition. The treatment may comprise concentrating the crude acesulfame potassium composition to form a water stream and an intermediate acesulfame potassium composition comprising acesulfame potassium and low amounts of acetoacetamide and then separating the intermediate acesulfame potassium composition to form the finished acesulfame potassium composition comprising acesulfame potassium and low amounts of acetoacetamide. As noted above, the crude acesulfame potassium composition may be formed by reacting sulfamic acid and an amine to form an amidosulfamic acid salt and then reacting the amidosulfamic acid salt with an acetoacetylating agent to form an acetoacetamide salt. The acetoacetamide salt may then be cyclized, hydrolyzed, and neutralized (and optionally phase separated). These steps are described in more detail below.

Importantly, in some embodiments, certain parameters of the concentrating and/or the separating operations are maintained at particular levels and/or within particular ranges. In some cases, the temperatures at which the concentrating and/or the separating operations are conducted are maintained at low levels. Also, in some embodiments, the residence times (of the crude acesulfame potassium composition in the concentrating operation or of the intermediate acesulfame potassium composition in the separating operation) are maintained at a low level. As a result, without being bound by theory, little or no additional impurities, e.g., acetoacetamide, are generated during treatment, e.g., during the concentrating and/or separating operations, which advantageously provides for a more pure finished acesulfame potassium composition. In some cases, the weight percentage of acetoacetamide in the finished acesulfame potassium composition or in the intermediate acesulfame potassium composition is less than the weight percentage of acetoacetamide in the crude acesulfame potassium composition, i.e., acetoacetamide content is actually reduced during treatment.

In some embodiments, the concentrating operation, e.g., one or more of the steps that make up the concentrating operation, is conducted at or maintained at a low temperature, e.g., a temperature below 90° C., e.g., below 88° C., below 85° C., below 83° C., below 80° C., below 78° C., below 75° C., below 73° C., below 70° C., below 65° C., below 55° C., below 50° C., or below 46° C. In some cases, the temperature of the concentrating operation may be maintained at a temperature above 0° C., e.g., above 10° C., above 15° C., above 20° C., above 22° C., above 25° C., above 35° C., above 40° C. or above 50° C. In terms of ranges, the temperature of the concentrating operation may range from 0° C. to 90° C., e.g., 25° C. to 90° C., from 55° C. to 90° C., from 10° C. to 88° C., from 10° C. to 85° C., from 75° C. to 88° C., from 80° C. to 88° C., from 15° C. to 85° C., from 75° C. to 85° C., from 20° C. to 83° C., from 20° C. to 80° C., from 22° C. to 78° C., from 25° C. to 75° C., from 25° C. to 73° C., from 15° C. to 50° C., from 25° C. to 65° C., from 22° C. to 50° C., from 20° C. to 55° C., from 25° C. to 70° C., or from 30° C. to 60° C.

In some embodiments, the separating operation, e.g., one or more of the steps that make up the separating operation, is conducted at or maintained at a low temperature, e.g., a temperature below 35° C., below 30° C., below 25° C., below 20° C., below 15° C., below 10° C., below 8° C., below 6° C., below 5° C., or below 0° C. In some cases, the temperature of the separating operation may be maintained at a temperature above −25° C., e.g., above −10° C., above 0° C., above 5° C., above 10° C., above 15° C., above 25° C., or above 30° C. In terms of ranges, the temperature of the separating operation may range from −25° C. to 35° C., e.g., −10° C. to 35° C., from 0° C. to 35° C., from 5° C. to 30° C., from −10° C. to 30° C., from −10° C. to 25° C., from −10° C. to 20° C., from −10° C. to 15° C., from 0° C. to 25° C., or from −10° C. to 30° C. The employment of the aforementioned temperatures in the treatment advantageously improves final product purity.

In some embodiments, the concentrating operation, e.g., one or more of the steps that make up the concentrating operation, is conducted at or maintained at a low residence time. In one embodiment, residence time is less than 180 minutes, e.g., less than 170 minutes, less than 150 minutes, less than 120 minutes, less than 100 minutes, less than 90 minutes, less than 75 minutes, less than 50 minutes, less than 40 minutes, less than 30 minutes, less than 20 minutes, or less than 10 minutes. In terms of lower limits, residence time may be at least 1 second, e.g., at least 10 seconds, at least 1 minute, at least 10 minutes, or at least 15 minutes. In terms of ranges, the residence time may range from 1 second to 180 minutes, e.g., from 10 seconds to 180 minutes, from 1 minute to 180 minutes, from 10 minutes to 150 minutes, from 1 minute to 50 minutes, from 1 minute to 30 minutes, from 10 minutes to 100 minutes, from 1 minute to 80 minutes, from 10 minutes to 80 minutes, from 10 minutes to 50 minutes, from 15 minutes to 90 minutes, or from 15 minutes to 75 minutes. The same residence time limits and ranges are applicable to the separating operation, e.g., one or more of the steps that make up the separating operation. The employment of residence times in the concentrating operation and/or separating operation advantageously improves final product purity.

In some embodiments, the concentrating operation, e.g., one or more of the steps that make up a concentrating operation, is conducted at or maintained at a low pH. In one embodiment, the pH of the separating is maintained below 10.0, e.g., below 9.5, below 9.0, below 8.5, below 8.0, below 7.5, below 7.0, or below 6.5. In terms of ranges, the pH of the concentrating operation is preferably maintained between 6.0 and 10.0, e.g., between 6.5 and 9.5, between 7.0 and 9.0, or between 7.5 and 8.5. The same pH limits and ranges are applicable to the separating operation, e.g., one or more of the steps that make up the separating operation. The employment of low pH levels in the concentrating operation or separating operation advantageously improves final product purity.

In cases where evaporation is utilized in the concentrating operation, the evaporation may be conducted at the aforementioned temperature limits and ranges. It has been discovered that, in addition to the aforementioned impurity reduction benefits, the utilization of lower evaporation temperatures surprisingly limits or eliminates the formation of solids in the evaporator, e.g., solid acesulfame potassium, which can lead to safety issues, e.g., unnecessary pressure build-up or explosion of the evaporator.

The aforementioned parameter limits and ranges are applicable to individual concentrating or separating operations that may make up the overall concentrating or separating operation. For example, if the concentrating operation may comprise evaporation, then the evaporation may be conducted at a temperature below 90° C., e.g., below 88° C., below 85° C., below 83° C., below 80° C., below 78° C., below 75° C., below 73° C., below 70° C., below 65° C., below 55° C., below 50° C., or below 46° C. As another example, if the concentrating operation may comprise evaporation, then the evaporation may be conducted at a residence time less than 180 minutes, e.g., less than 170 minutes, less than 150 minutes, less than 120 minutes, less than 100 minutes, less than 90 minutes, less than 75 minutes, less than 50 minutes, less than 40 minutes, less than 30 minutes, less than 20 minutes, or less than 10 minutes. As another example, if the separating operation comprises crystallization, then the crystallization may be conducted at a pH below 10.0, e.g., below 9.5, below 9.0, below 8.5, below 8.0, below 7.5, below 7.0, or below 6.5.

By performing the treatment under the temperature, pH, and/or residence time parameters discussed herein, stress on the acesulfame potassium molecules (in the crude acesulfame potassium composition) is advantageously minimized during the separating operation. As a result, less acesulfame potassium degrades into the acetoacetamide during the separating operation. Thus, the intermediate acesulfame potassium product and the finished acesulfame potassium composition advantageously contain lower amounts of impurities, e.g., acetoacetamide (if any) than would typically form from acesulfame potassium degradation.

The concentrating operation, in some embodiments, comprises the step of evaporating the crude acesulfame potassium composition to form a water stream and an intermediate acesulfame potassium composition comprising acesulfame potassium and less than 75 wt % water, e.g., less than 50 wt %, less than 40 wt %, less than 30 wt %, less than 20 wt %, less than 15 wt %, less than 10 wt %, less than 50 wt %, less than 3 wt %, or less than 1 wt %. The water stream may refer to water that is evaporated from the crude acesulfame potassium composition, e.g., water that is not present in the intermediate acesulfame potassium composition. The evaporating may be conducted at the concentrating operation parameters mentioned herein.

In some cases, the separating comprises the step of crystallizing the intermediate acesulfame potassium composition or a derivative thereof, to form the finished acesulfame potassium composition, which may be in the form of acesulfame potassium crystals (or a composition/stream comprising a the acesulfame potassium crystals). The intermediate acesulfame potassium composition may be a stream or a composition that results from the concentration of the crude acesulfame potassium composition. The crystallizing may be conducted at the separating operation parameters mentioned herein.

In some embodiments the separating comprises the step of filtering the intermediate acesulfame potassium composition (or a crystal-containing derivative thereof) to form the finished acesulfame potassium composition. A crystal-containing derivative of the intermediate acesulfame potassium composition may be a stream or a composition that results from the concentration of the crude acesulfame potassium composition and that contains crystals either in dissolved or solid form. The filtering may be conducted at the separating operation parameters mentioned herein.

In preferred embodiments, the overall treatment comprises the steps of evaporating the crude acesulfame potassium composition to form a water stream and the intermediate acesulfame potassium composition comprising acesulfame potassium and low amounts of water (see limits/ranges above), crystallizing the intermediate acesulfame potassium composition to form acesulfame potassium crystals, and filtering the acesulfame potassium crystals to form the finished acesulfame potassium composition.

In one embodiment, the process comprises the steps of providing the crude acesulfame potassium composition comprising acesulfame potassium and acetoacetamide and water and evaporating the crude acesulfame potassium composition to form the water stream and the intermediate acesulfame potassium composition (as disclosed above). In this embodiment, the residence time of the crude acesulfame potassium composition in the evaporator is less than 180 minutes, e.g., less than 170 minutes, less than 150 minutes, less than 120 minutes, less than 100 minutes, less than 90 minutes, less than 75 minutes, less than 50 minutes, less than 40 minutes, less than 30 minutes, less than 20 minutes, or less than 10 minutes. In terms of ranges, the residence time may range from 1 second to 180 minutes, e.g., from 10 seconds to 180 minutes, from 1 minute to 180 minutes, from 10 minutes to 150 minutes, from 10 minutes to 100 minutes, from 10 minutes to 80 minutes, from 10 minutes to 50 minutes, from 15 minutes to 90 minutes, or from 15 minutes to 75 minutes.

In some embodiments, the forming of the finished acesulfame potassium composition from the intermediate acesulfame potassium composition comprises crystallizing the intermediate acesulfame potassium composition to form acesulfame potassium crystals and filtering the crystal-containing stream to form the finished acesulfame potassium composition. In preferred embodiments, a falling film evaporator is employed to form the intermediate acesulfame potassium composition.

The crude acesulfame composition may further comprise solvent, and in some embodiments, the concentrating operation comprises a solvent removal step, e.g., stripping solvent from the crude acesulfame potassium composition, e.g., prior to concentrating (evaporating). The process may comprise the steps of providing the crude acesulfame potassium composition, stripping the crude acesulfame potassium composition to form a solvent stream comprising solvent and a stripped acesulfame potassium composition comprising less than 50 wt % solvent, e.g., less than 40 wt %, less than 30 wt %, less than 20 wt %, less than 15 wt %, less than 10 wt %, less than 50 wt %, less than 3 wt %, or less than 1 wt %, followed by the aforementioned concentrating operation and separating operation. It has been found that removal of solvent, e.g., methylene dichloride, surprisingly increases concentration efficiency. In addition to the stripping step, the separating operation may further comprise the evaporation, crystallization, and/or filtration steps.

In some embodiments, the separating operation comprises the step of crystallizing the intermediate acesulfame potassium composition to form a crystal-containing stream comprising acesulfame potassium crystals. The crystallization may be conducted at the pH ranges and limits discussed above. The process may further comprise the step of forming from the crystal-containing stream the finished acesulfame potassium composition. In some embodiments, the forming step comprises filtering the crystal-containing stream to form the finished acesulfame potassium composition. This embodiment may also utilize the aforementioned solvent stripping step.

If filtration is employed in the separating operation, the filtration is preferably conducted at the separating operation temperature limits and ranges discussed herein. In cases where crystallization is utilized in the separating operation, the crystallization may be conducted at the temperature limits and ranges discussed herein.

In addition to the temperature limits and ranges, the crystallization may be conducted at the pH limits and ranges discussed herein. For example, the crystallization may be conducted at a pH below 10.0, e.g., below 9.5, below 9.0, below 8.5, below 8.0, below 7.5, below 7.0, or below 6.5. In addition to the benefits of reducing acetoacetamide formation, it has also been found that conducting the crystallization also improves separation of dimers that may form in side reaction. It is postulated that the lower pH levels promote precipitation of dimers. Higher pH levels have been found to promote dimer solubility. The precipitation advantageously provides for more efficient separation thereof.

In addition to the temperature limits and ranges, the crystallization may be conducted at the residence time limits and ranges discussed herein.

In one embodiment, the provision of the crude acesulfame potassium composition (which is subsequently concentrated and separated) comprises the steps of reacting sulfamic acid and an amine to form an amidosulfamic acid salt and reacting the amidosulfamic acid salt with the acetoacetylating agent to form the acetoacetamide salt. The acetoacetamide salt may then be reacted with a cyclizing agent, optionally in the presence of a solvent, to form the cyclic (sulfur trioxide) adduct composition. In preferred embodiments, the provision of the crude acesulfame potassium composition further comprises the step of hydrolyzing the cyclic sulfur trioxide adduct to form acesulfame-H, and neutralizing the acesulfame-H to form the crude acesulfame potassium composition. In some embodiments, the neutralizing step comprises reacting the acesulfame-H (optionally in the acesulfame-H composition) with a neutralizing agent to form the acesulfame potassium composition. The reacting may comprise contacting the acesulfame-H with the neutralizing agent. The acesulfame potassium composition comprises acesulfame potassium and impurities. The formation of the cyclic sulfur trioxide adduct may yield a cyclic sulfur trioxide adduct composition that comprises the cyclic sulfur trioxide adduct and additional reaction side products and impurities. Similarly, the formation of the acesulfame-H may yield an acesulfame-H composition that comprises acesulfame-H and additional reaction side products and impurities.

The specific methods employed to implement the desired temperature and/or residence time features may vary widely. With regard to temperature, heat exchange equipment, e.g., cooling equipment, may be employed. Temperature maintenance methods are well known in the art.

With regard to residence time, the respective separation streams may be controlled to maintain the residence times discussed herein using the appropriate valves, gauges, metering devices, and piping.

The acesulfame potassium composition formed via the process(es) described herein will be a high purity acesulfame potassium composition. For example, the acesulfame potassium composition may comprise acetoacetamide salts in the amounts discussed above.

Acesulfame Potassium Compositions

The crude acesulfame potassium composition is formed by hydrolyzing a cyclic sulfur trioxide adduct to form an acesulfame-H composition and neutralizing the acesulfame-H in the acesulfame-H composition to form the crude acesulfame potassium composition, as discussed herein. The product of the neutralization step is phase separated into aqueous and organic phases. The crude acesulfame potassium composition may be obtained from the aqueous phase (without any further purification). The crude acesulfame potassium composition comprises acesulfame potassium and acetoacetamide, e.g., less than 2800 wppm acetoacetamide, e.g., less than 2700 wppm, less than 2600 wppm, less than 2500 wppm, less than 2400 wppm, less than 2000 wppm, less than 1500 wppm, less than 1000 wppm, less than 500 wppm, or less than 100 wppm. In some cases the crude acesulfame potassium composition is substantially free of acetoacetamide (undetectable), e.g., free of acetoacetamide. In terms of ranges, the crude acesulfame potassium composition may comprise from 1 wppm to 2800 wppm acetoacetamide, e.g., from 1 wppm to 2700 wppm, from 10 wppm to 2700 wppm, from 20 wppm to 2500 wppm, from 100 wppm to 2500 wppm, from 500 wppm to 2500 wppm, from 1500 to 2400 wppm, from 500 wppm to 2375 wppm, from 600 wppm to 2000 wppm, from 900 wppm to 1900 wppm, from 300 wppm to 1500 wppm, from 400 wppm to 1400 wppm, from 600 wppm to 1200 wppm or from 700 wppm to 1100 wppm.

The crude acesulfame potassium composition may further comprise acetoacetamide-N-sulfonic acid, which may be present in the amounts discussed above with respect to acetoacetamide.

The finished acesulfame potassium compositions, which are typically suitable for end consumer usage, are formed by treating the crude acesulfame potassium composition to remove impurities, as discussed herein. This finished acesulfame potassium composition preferably comprises a mixture of acesulfame potassium and less than 33 wppm acetoacetamide, e.g., less than 32 wppm, less than 30 wppm, less than 25 wppm, less than 20 wppm, less than 15 wppm, less than 12 wppm, less than 10 wppm, less than 7 wppm, less than 5 wppm, less than 3 wppm, less than 1 wppm, less than 0.8 wppm, less than 0.5 wppm, or less than 0.3 wppm. In some cases the finished acesulfame potassium composition is substantially free of acetoacetamide, e.g., free of acetoacetamide. In terms of ranges, the finished acesulfame potassium composition may comprise from 1 wppb to 33 wppm acetoacetamide, e.g., from 10 wppb to 32 wppm, from 10 wppb to 25 wppm, from 10 wppb to 15 wppm, from 10 wppb to 12 wppm, from 10 wppb to 10 wppm, from 10 wppb to 7 wppm, from 10 wppb to 5 wppm, from 10 wppb to 3 wppm, from 100 wppb to 15 wppm, from 100 wppb to 10 wppm, or from 100 wppb to 5 wppm.

The finished acesulfame potassium composition preferably comprises acesulfame potassium and less than 33 wppm acetoacetamide-N-sulfonic acid, e.g., less than 32 wppm, less than 30 wppm, less than 25 wppm, less than 20 wppm, less than 15 wppm, less than 12 wppm, less than 10 wppm, less than 7 wppm, less than 5 wppm, less than 3 wppm, less than 1 wppm, less than 0.8 wppm, less than 0.5 wppm, or less than 0.3 wppm. In some cases the finished acesulfame potassium composition is substantially free of acetoacetamide-N-sulfonic acid, e.g., free of acetoacetamide-N-sulfonic acid. In terms of ranges, the finished acesulfame potassium composition may comprise from 1 wppb to 33 wppm acetoacetamide-N-sulfonic acid, e.g., from 10 wppb to 32 wppm, from 10 wppb to 25 wppm, from 1 wppb to 22 wppm, from 10 wppb to 22 wppm, from 1 wppb to 20 wppm, from 10 wppb to 20 wppm, from 10 wppb to 15 wppm, from 10 wppb to 12 wppm, from 10 wppb to 10 wppm, from 10 wppb to 7 wppm, from 10 wppb to 5 wppm, from 10 wppb to 3 wppm, from 100 wppb to 15 wppm, from 100 wppb to 10 wppm, or from 100 wppb to 5 wppm.

The acetoacetamide-N-sulfonic acid and/or the acetoacetamide content may be measured in the crude, intermediate, or finished acesulfame potassium compositions via high performance liquid chromatography (HPLC) analysis, based on European Pharmacopoeia guidelines for thin layer chromatography (2017) and adapted for HPLC. A particular measurement scenario utilizes an LC Systems HPLC unit from Shimadzu having a CBM-20 Shimadzu controller and being equipped with an IonPac NS1 ((5 µm) 150×4 mm) analytical column and an IonPac NG1 guard column (35×4.0 mm). A Shimadzu SPD-M20A photodiode array detector can be used for detection (at 270 nm and 280 nm wavelength). Analysis may be performed at 23° C. column temperature. As a first eluent solution, an aqueous mixture of tetra butyl ammonium hydrogen sulfate (3.4 g/L), acetonitrile (300 mL/L), and potassium hydroxide (0.89 g/L) may be employed; as a second eluent solution, an aqueous mixture of tetra butyl ammonium hydrogen sulfate (3.4 g/L) and potassium hydroxide (0.89 g/L) may be employed. Elution may be conducted in gradient mode according to the following second eluent flow profile:

0 to 3 minutes: constant 80% (v/v)
3 to 6 minutes: linear reduction to 50% (v/v)
6 to 15 minutes: constant at 50% (v/v)
15 to 18 minutes: linear reduction to 0%
18 to 22 minutes: constant at 0%
22 to 24 minutes: linear increase to 80% (v/v)
24 to 35 minutes constant at 80% (v/v).

Overall flow rate of eluent may be approximately 1.2 mL/min. The data collection and calculations may be performed using Lab Solution software from Shimadzu.

One or more intermediate acesulfame potassium compositions may be formed, e.g., during the concentrating operation, for example via evaporation. The intermediate acesulfame potassium composition preferably comprises a mixture of acesulfame potassium and less than 33 wppm acetoacetamide, e.g., less than 30 wppm, less than 25 wppm, less than 20 wppm, less than 15 wppm, less than 12 wppm, less than 10 wppm, less than 7 wppm, less than 5 wppm, less than 3 wppm, less than 1 wppm, less than 0.8 wppm, less than 0.5 wppm, or less than 0.3 wppm. In some cases the intermediate acesulfame potassium composition is free of acetoacetamide, e.g., substantially free of acetoacetamide (undetectable). In terms of ranges, the intermediate acesulfame potassium composition may comprise from 1 wppb to 33 wppm acetoacetamide, e.g., from 10 wppb to 30 wppm, from 10 wppb to 25 wppm, from 10 wppb to 15 wppm, from 10 wppb to 12 wppm, from 10 wppb to 10 wppm, from 10 wppb to 7 wppm, from 10 wppb to 5 wppm, from 10 wppb to 3 wppm, from 100 wppb to 15 wppm, from 100 wppb to 10 wppm, from 100 wppb to 5 wppm. The intermediate acesulfame potassium composition may comprise a mixture of acesulfame potassium and acetoacetamide.

As noted above, the crude acesulfame potassium composition is formed by the aforementioned reactions, hydrolysis, and neutralization. The crude acesulfame potassium composition is concentrated to form the intermediate acesulfame composition, which is then separated to form the finished acesulfame potassium composition, as discussed herein. In preferred embodiments, the temperature at which the concentrating operation, e.g., the evaporation, is conducted is at or below 90° C., e.g., below 88° C., below 85° C., below 83° C., below 80° C., below 78° C., below 75° C., below 73° C., below 70° C., below 65° C., below 55° C., below 50° C., or below 46° C. (optionally at a temperature ranging from 0° C. to 90° C., e.g., 25° C. to 90° C., from 55° C. to 90° C., from 10° C. to 88° C., from 10° C. to 85° C., from 75° C. to 88° C., from 80° C. to 88° C., from 15° C. to 85° C., from 75° C. to 85° C., from 20° C. to 83° C., from 20° C. to 80° C., from 22° C. to 78° C., from 25° C. to 75° C., from 25° C. to 73° C., from 15° C. to 50° C., from 25° C. to 65° C., from 22° C. to 50° C., from 20° C. to 55° C., from 25° C. to 70° C., or from 30° C. to 60° C.); the concentrating operation utilizes a residence time less than 180 minutes, e.g., less than 170 minutes, less than 150 minutes, less than 120 minutes, less than 100 minutes, less than 90 minutes, less than 75 minutes, less than 50 minutes, less than 40 minutes, less than 30 minutes, less than 20 minutes, or less than 10 minutes (optionally utilizing a residence time ranging from 1 second to 180 minutes, e.g., from 10 seconds to 180 minutes, from 1 minute to 180 minutes, from 10 minutes to 150 minutes, from 1 minute to 50 minutes, from 1 minute to 30 minutes, from 10 minutes to 100 minutes, from 10 minutes to 80 minutes, from 10 minutes to 50 minutes, from 15 minutes to 90 minutes, or from 15 minutes to 75 minutes); the temperature at which the separating operation, e.g., the crystallization and/or filtration, is conducted is below 35° C., e.g., below 30° C., below 25° C., below 20° C., below 15° C., below 10° C., below 8° C., below 6° C., below 5° C., or below 0° C. (optionally at a temperature ranging from −25° C. to 35° C., e.g., −10° C. to 35° C., from 0° C. to 35° C., from 5° C. to 30° C., from −10° C. to 30° C., from −10° C. to 25° C., from −10° C. to 20° C., from −10° C. to 15° C., from 0° C. to 25° C., or from −10° C. to 30° C.); the separating operation utilizes a residence time less than 180 minutes, e.g., less than 170 minutes, less than 150 minutes, less than 120 minutes, less than 100 minutes, less than 90 minutes, less than 75 minutes, less than 50 minutes, less than 40 minutes, less than 30 minutes, less than 20 minutes, or less than 10 minutes (optionally utilizing a residence time ranging from 1 second to 180 minutes, e.g., from 10 seconds to 180 minutes, from 1 minute to 180 minutes, from 10 minutes to 150 minutes, from 10 minutes to 100 minutes, from 1 minute to 80 minutes, from 10 minutes to 80 minutes, from 10 minutes to 50 minutes, from 15 minutes to 90 minutes, or from 15 minutes to 75 minutes); the crude acesulfame potassium composition may comprise less than 2800 wppm acetoacetamide, e.g., less than 2700 wppm, less than 2600 wppm, less than 2500 wppm, less than 2400 wppm, less than 2000 wppm, less than 1500 wppm, less than 1000 wppm, less than 500 wppm, or less than 100 wppm (optionally from 1 wppm to 2800 wppm acetoacetamide, e.g., from 1 wppm to 2800 wppm, from 10 wppm to 2700 wppm, from 20 wppm to 2500 wppm, from 100 wppm to 2500 wppm, from 500 wppm to 2500 wppm, from 1500 to 2400 wppm, from 500 wppm to 2375 wppm, from 600 wppm to 2000 wppm, from 900 to 1900 wppm, from 300 wppm to 1500 wppm, from 400 wppm to 1400 wppm, from 600 wppm to 1200 wppm or from 700 wppm to 1100 wppm) (the crude acesulfame potassium composition may comprise acetoacetamide-N-sulfonic acid in the same amounts); the intermediate acesulfame potassium composition may comprise less than 33 wppm acetoacetamide, e.g., less than 32 wppm, less than 30 wppm, less than 25 wppm, less than 20 wppm, less than 15 wppm, less than 12 wppm, less than 10 wppm, less than 7 wppm, less than 5 wppm, less than 3 wppm, less than 1 wppm, less than 0.8 wppm, less than 0.5 wppm, or less than 0.3 wppm (optionally from 1 wppb to 33 wppm acetoacetamide, e.g., from 10 wppb to 32 wppm, from 10 wppb to 25 wppm, from 10 wppb to 15 wppm, from 10 wppb to 12 wppm, from 10 wppb to 10 wppm, from 10 wppb to 7 wppm, from 10 wppb to 5 wppm, from 10 wppb to 3 wppm, from 100 wppb to 15 wppm, from 100 wppb to 10 wppm, from 100 wppb to 5 wppm) (the intermediate acesulfame potassium composition may comprise acetoacetamide-N-sulfonic acid in the same amounts); and the finished acesulfame potassium composition may comprise less than 33 wppm acetoacetamide, e.g., less than 32 wppm, less than 30 wppm, less than 25 wppm, less than 20 wppm, less than 15 wppm, less than 12 wppm, less than 10 wppm, less than 7 wppm, less than 5 wppm, less than 3 wppm, less than 1 wppm, less than 0.8 wppm, less than 0.5 wppm, or less than 0.3 wppm (optionally from 1 wppb to 33 wppm acetoacetamide, e.g., from 10 wppb to 32 wppm, from 10 wppb to 25 wppm, from 10 wppb to 15 wppm, from 10 wppb to 12 wppm, from 10 wppb to 10 wppm, from 10 wppb to 7 wppm, from 10 wppb to 5 wppm, from 10 wppb to 3 wppm, from 100 wppb to 15 wppm, from 100 wppb to 10 wppm, from 100 wppb to 5 wppm) (the finished acesulfame potassium composition may comprise acetoacetamide-N-sulfonic acid in the same amounts).

In a particular embodiment, the concentrating operation, e.g., the evaporation, is conducted at a temperature below 85° C., the intermediate acesulfame potassium composition comprises from 1 wppb to 33 wppm acetoacetamide (and optionally less than 33 wppm acetoacetamide-N-sulfonic acid), and the finished acesulfame potassium composition comprises less than 33 wppm acetoacetamide (and optionally less than 33 wppm acetoacetamide-N-sulfonic acid).

In another particular embodiment, the concentrating operation, e.g., the evaporation, is conducted at a temperature below 60° C., the evaporator residence time is less than 50 minutes and the intermediate acesulfame potassium composition comprises from 10 wppb to 25 wppm acetoacetamide (and optionally less than 30 wppm acetoacetamide-N-sulfonic acid), and the finished acesulfame potassium composition comprises from 10 wppb to 15 wppm acetoacetamide (and optionally less than 30 wppm acetoacetamide-N-sulfonic acid).

In another particular embodiment, the concentrating operation, e.g., the evaporation, is conducted at a temperature below 46° C., the evaporator residence time is less than 30 minutes, the crystallizing is conducted at a temperature below 35° C., the intermediate acesulfame potassium composition comprises from 10 wppb to 12 wppm acetoacetamide (and optionally less than 20 wppm acetoacetamide-N-sulfonic acid), and the finished acesulfame potassium composition comprises from 10 wppb to 7 wppm acetoacetamide.

In another particular embodiment, the concentrating operation, e.g., the evaporation, is conducted at a temperature ranging from 25° C. to 90° C., evaporator residence time ranges from 10 seconds to 180 minutes, the separating operation, e.g., the crystallization and/or filtration, is conducted at a temperature ranging from −10° C. to 35° C., the separating operation residence time ranges from 10 seconds to 180 minutes, the crude acesulfame potassium composition comprises 1 wppm to 2800 wppm acetoacetamide and 1 wppm to 2800 wppm acetoacetamide-N-sulfonic acid, the intermediate acesulfame potassium composition comprises 1 wppb to 33 wppm acetoacetamide and 1 wppb to 33 wppm acetoacetamide-N-sulfonic acid, and the finished acesulfame potassium composition comprises 1 wppb to 33 wppm acetoacetamide, and 1 wppb to 33 wppm acetoacetamide-N-sulfonic acid.

In another particular embodiment, the concentrating operation, e.g., the evaporation, is conducted at a temperature ranging from 25° C. to 90° C., evaporator residence time ranges from 10 seconds to 180 minutes, the separating operation, e.g., the crystallization and/or filtration, is conducted at a temperature ranging from −10° C. to 35° C., the separating operation residence time ranges from 10 seconds to 180 minutes, the crude acesulfame potassium composition comprises 1 wppm to 2800 wppm acetoacetamide and 1 wppm to 2800 wppm acetoacetamide-N-sulfonic acid, the intermediate acesulfame potassium composition comprises 1 wppb to 33 wppm acetoacetamide and 1 wppb to 33 wppm acetoacetamide-N-sulfonic acid, and the finished acesulfame potassium composition comprises 1 wppb to 33 wppm acetoacetamide, and 1 wppb to 33 wppm acetoacetamide-N-sulfonic acid.

In another particular embodiment, the concentrating operation, e.g., the evaporation, is conducted at a temperature ranging from 20° C. to 55° C., evaporator residence time ranges from 1 minute to 300 minutes, the separating operation, e.g., the crystallization and/or filtration, is conducted at a temperature ranging from −10° C. to 15° C., the separating operation residence time ranges from 1 to 180 minutes, the crude acesulfame potassium composition comprises from 500 wppm to 2375 wppm acetoacetamide, the intermediate acesulfame potassium composition comprises 10 wppb to 20 wppm acetoacetamide and 10 wppb to 20 wppm acetoacetamide-N-sulfonic acid, and the finished acesulfame potassium composition comprises from 10 wppb to 10 wppm acetoacetamide, and from 1 wppb to 20 wppm acetoacetamide-N-sulfonic acid.

The acesulfame potassium compositions (crude and/or finished) may, in some cases, comprise organic impurities. Organic impurities include, inter alia, halo-acesulfame potassium. The acesulfame potassium compositions (crude and/or finished) also may comprise heavy metals. The organic impurities and/or heavy metals may be present in an amount ranging from 1 wppb to 25 wppm, based on the total weight of the respective acesulfame potassium composition, crude or finished, e.g., from 100 wppb to 20 wppm, from 100 wppb to 15 wppm, from 500 wppb to 10 wppm, or from 1 wppm to 5 wppm. Heavy metals are defined as metals with relatively high densities, e.g., greater than 3 g/cm$^3$ or greater than 7 g/cm$^3$. Exemplary heavy metals include lead and mercury. In some cases, the crude or finished acesulfame potassium composition may comprise mercury in an amount ranging from 1 wppb to 25 wppm, e.g., from 100 wppb to 20 wppm, from 100 wppb to 15 wppm, from 500 wppb to 10 wppm, or from 1 wppm to 5 wppm. In terms of limits, the crude or finished acesulfame potassium composition may comprise less than 25 wppm mercury, e.g., less than 20 wppm, less than 15 wppm, less than 10 wppm, or less than 5 wppm. In some cases, the crude or finished acesulfame potassium composition may comprise lead in an amount ranging from 1 wppb to 25 wppm, e.g., from 100 wppb to 20 wppm, from 100 wppb to 15 wppm, from 500 wppb to 10 wppm, or from 1 wppm to 5 wppm. In terms of limits, the crude or finished acesulfame potassium composition may comprise less than 25 wppm lead, e.g., less than 20 wppm, less than 15 wppm, less than 10 wppm, or less than 5 wppm. In some cases, when potassium hydroxide is formed via a membrane process, the resultant crude or finished acesulfame potassium composition may have very low levels of mercury, if any, e.g., less than 10 wppm, less than 5 wppm, less than 3 wppm, less than 1 wppm, less than 500 wppb, or less than 100 wppb.

Intermediate Reaction Parameters

The reactions for production of high purity acesulfame potassium are described in more detail below.

Amidosulfamic Acid Salt Formation Reaction

In a first reaction step, sulfamic acid and an amine are reacted to form sulfamic acid salt. An exemplary reaction scheme that employs triethylamine as the amine and yields triethyl ammonium sulfamic acid salt is shown in reaction (1), below.

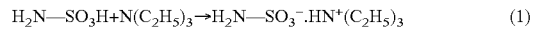
$$H_2N\text{---}SO_3H+N(C_2H_5)_3 \rightarrow H_2N\text{---}SO_3^-.HN^+(C_2H_5)_3 \qquad (1)$$

Acetic acid is also present in the first reaction mixture and reacts with the amine, e.g., triethylamine, to form a triethylammonium acetate, as shown in reaction (2), below.

$$H_3C\text{---}COOH+N(C_2H_5)_3 \rightarrow H_3C\text{---}COO^-.HN^+(C_2H_5)_3 \qquad (2)$$

The amine employed in these reactions may vary widely. Preferably, the amine comprises triethylamine. In one embodiment, the amine may be selected from the group consisting of trimethylamine, diethylpropylamine, tri-n-propylamine, triisopropylamine, ethyldiisopropylamine, tri-n-butylamine, triisobutylamine, tricyclohexylamine, ethyldicyclohexylamine, N,N-dimethylaniline, N,N-diethylaniline, benzyldimethylamine, pyridine, substituted pyridines such as picoline, lutidine, cholidine or methylethylpyridine, N-methylpiperidine, N-ethylpiperidine, N-methylmorpholine, N,N-dimethylpiperazine, 1,5-diazabicyclo[4.3.0]-non-5-en, 1,8-diazabicyclo-[5.4.0]-undec-7-en, 1,4-diazabicyclooctane, tetramethylhexamethylendiamine, tetramethylethylendiamine, tetramethylpropylendiamine, tetramethylbutylendiamine, 1,2-dimorpholylethan, pentamethyldiethyltriamine, pentaethyldiethylentriamine, pentamethyldipropylentriamine, tetramethyldiaminomethane, tetrapropyldiaminomethane, hexamethyltriethylentetramine, hexamethyltripropylenetetramine, diisobutylentriamine, triisopropylentriamine, and mixtures thereof.

Acetoacetamide Salt Formation Reaction

Once formed in reaction (1), the sulfamic acid salt is reacted with the acetoacetylating agent to form the acetoacetamide salt, preferably acetoacetamide-N-sulfonate triethylammonium salt. Preferably, the acetoacetylating agent comprises diketene, although other acetoacetylating agents may be employed, either with or without diketene.

In one embodiment, the resultant acetoacetamide salt corresponds to the following formula (3).

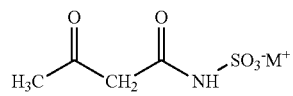
(3)

wherein $M^+$ is an appropriate ion. Preferably, $M^+$ is an alkali metal ion or $N^+R_1R_2R_3R_4$. $R_1$, $R_2$, $R_3$ and $R_4$, independently of one another, may be organic radicals or hydrogen, preferably H or $C_1$-$C_8$ alkyl, $C_6$-$C_{10}$ cycloalkyl, aryl and/or aralkyl. In a preferred embodiment, $R_1$ is hydrogen, and $R_2$, $R_3$ and $R_4$ are alkyl, e.g., ethyl.

An exemplary reaction scheme for forming an acetoacetamide salt employs a trialkyl ammonium amidosulfamic acid salt and diketene as reactants and yields an acetoacetamide triethylammonium salt is shown in reaction (4), below.

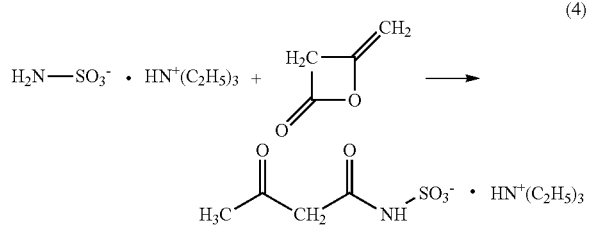
(4)

In one embodiment, the reaction is conducted in the presence of a catalyst, which may vary widely. In some embodiments, the catalyst comprises one or more amines and/or phosphines. Preferably, the catalyst comprises triethylamine. In some cases trimethylamine serves as both a catalyst and a reactant.

In one embodiment, wherein the amidosulfamic acid salt formation reaction and the acetoacetamide salt formation reaction are conducted in separate reactors, a second reaction mixture comprises the amidosulfamic acid salt, the diketene, and the catalyst, e.g., triethylamine. Preferably, catalyst from the first reaction is carried through to the reaction mixture of the second reaction. The second reaction mixture is then subjected to conditions effective to form the acetoacetamide salt.

In one embodiment, the composition of the second reaction mixture may be similar to that of the first reaction mixture. In a preferred embodiment, the reaction product of the amidosulfamic acid salt formation reaction provides the amidosulfamic acid salt component of the second reaction mixture. In addition to the above-mentioned components, the second reaction mixture may further comprise reaction by-products from the first reaction or non-reacted starting materials.

In one embodiment, the amount of acetoacetylating agent, e.g., diketene, should be at least equimolar to the reactant amidosulfamic acid salt that is provided. In one embodiment, the process may utilize a diketene in excess, but preferably in an excess less than 30 mol %, e.g., less than 10 mol %. Greater excesses are also contemplated.

The amidosulfamic acid salt formation reaction and/or the acetoacetamide salt formation reaction may employ an organic solvent. Suitable inert organic solvents include any organic solvents that do not react in an undesired manner with the starting materials, cyclizing agent, final products and/or the catalysts in the reaction. The solvents preferably have the ability to dissolve, at least partially, amidosulfamic acid salts. Exemplary organic solvents include halogenated aliphatic hydrocarbons, preferably having up to 4 carbon atoms such as, for example, methylene chloride, chloroform, 1,2-dichlorethane, trichloroethylene, tetrachloroethylene, trichlorofluoroethylene; aliphatic ketones, preferably those having 3 to 6 carbon atoms such as, for example, acetone, methyl ethyl ketone; aliphatic ethers, preferably cyclic aliphatic ethers having 4 or 5 carbon atoms such as, for example, tetrahydrofuran, dioxane; lower aliphatic carboxylic acids, preferably those having 2 to 6 carbon atoms such as, for example, acetic acid, propionic acid; aliphatic nitriles, preferably acetonitrile; N-alkyl-substituted amides of carbonic acid and lower aliphatic carboxylic acids, preferably amides having up to 5 carbon atoms such as, for example, tetramethylurea, dimethylformamide, dimethylacetamide, N-methylpyrrolidone; aliphatic sulfoxides, preferably dimethyl sulfoxide, and aliphatic sulfones, preferably sulfolane.

Particularly preferred solvents include dichloromethane (methylene chloride), 1,2-dichloroethane, acetone, glacial acetic acid and dimethylformamide, with dichloromethane (methylene chloride) being particularly preferred. The solvents may be used either alone or in a mixture. In one embodiment, the solvent is a halogenated, aliphatic hydrocarbon solvent, preferably the solvent is dichloromethane. Chloroform and tetrachloromethane are also exemplary solvents.

In one embodiment, the acetoacetamide salt formation reaction is conducted a temperature ranging from −30° C. to 50° C., e.g., from 0° C. to 25° C. The reaction pressure may vary widely. In preferred embodiments, the reaction is carried out at atmospheric pressure, although other pressures are also contemplated. The reaction time may vary widely, preferably ranging from 0.5 hours to 12 hours, e.g., from 1 hour to 10 hours. In one embodiment, the reaction is carried out by introducing the amidosulfamic acid salt and metering in the diketene. In another embodiment, the reaction is carried out by introducing diketene and metering in the amidosulfamic acid salt. The reaction may be carried out by introducing the diketene and amidosulfamic acid and metering in the catalyst.

Once formed, each reaction product is optionally subjected to one or more purification steps. For example the solvent may be separated from the reaction product, e.g., via distillation, and the residue (mainly acetoacetamide-N-sulfonate) may be recrystallized from a suitable solvent such as, for example, acetone, methyl acetate or ethanol.

Cyclization and Hydrolyzation

The acetoacetamide salt is reacted with cyclizing agent, e.g., cyclizing agent in the cyclizing agent composition, in the presence of a solvent to form the cyclic (sulfur trioxide) adduct composition, which contains cyclic sulfur trioxide adduct and, in some cases, impurities. In some cases, a cooling step occurs before the cyclic sulfur trioxide adduct formation reaction. In one embodiment, the cyclization is achieved by using at least an equimolar amount of the cyclizing agent. The cyclizing agent may be dissolved in an inert inorganic or organic solvent. The cyclizing agent is generally used in a molar excess, e.g., up to a 20 fold excess, or up to a 10 fold excess, based on the total moles of acetoacetamide salt. An exemplary cyclization reaction using sulfur trioxide as the cyclizing agent is shown in reaction (5), below.

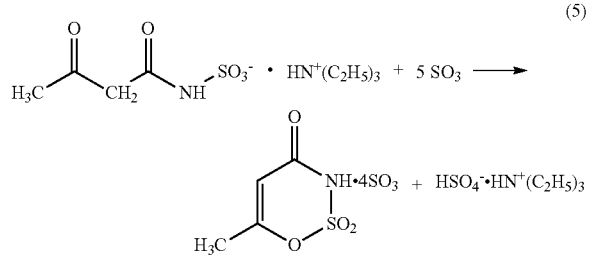

(5)

In one embodiment, the weight ratio of solvent to cyclizing agent in the cyclizing agent composition is at least 1:1, e.g., at least 2:1, or at least 5:1. In one embodiment, the weight ratio of solvent to cyclizing agent in the cyclizing agent composition ranges from 1:1 to 25:1, e.g., from 1:1 to 10:1, from 2:1 to 10:1, or from 5:1 to 10:1.

A cyclizing agent may be any compound that initiates the ring closure of the acetoacetamide salt. Although sulfur trioxide is a preferred cyclizing agent, the employment of other cyclizing agents is contemplated.

The cyclizing agent may be added to the reaction mixture either in the solid or the liquid form or by condensing in vapor. Suitable inert inorganic or organic solvents are those liquids which do not react in an undesired manner with sulfur trioxide or the starting materials or final products of the reaction. Preferred organic solvents include, but are not limited to, halogenated aliphatic hydrocarbons, preferably having up to four carbon atoms, such as, for example, methylene chloride (dichloromethane), chloroform, 1,2-dichloroethane, trichloroethylene, tetrachloroethylene, trichlorofluoroethylene; esters of carbonic acid with lower aliphatic alcohols, preferably with methanol or ethanol; nitroalkanes, preferably having up to four carbon atoms, in particular nitromethane; alkyl-substituted pyridines, preferably collidine; and aliphatic sulfones, preferably sulfolane. Particularly preferred solvents for the cyclization reaction include dichloromethane (methylene chloride), 1,2-dichloroethane, acetone, glacial acetic acid and dimethylformamide, with dichloromethane (methylene dichloride) being particularly preferred. Other solvents, e.g., other solvents mentioned herein, may also be suitable as solvents. The solvents may be used either alone or in a mixture. In one embodiment, the solvent is a halogenated, aliphatic hydrocarbon solvent, preferably the solvent is dichloromethane. The processes may employ these solvents alone or in mixtures thereof.

In some cases, the solvent in the cyclizing agent composition may be selected from 1) concentrated sulfuric acid, 2) liquid sulfur dioxide, or 3) an inert organic solvent.

In a preferred embodiment, the same solvent is used in both the acetoacetamide salt formation reaction and the cyclization reaction. As one benefit, the solution obtained in the acetoacetamide salt formation reaction, without isolation of the acetoacetamide salt formation reaction product, may be used immediately in the cyclization.

In one embodiment, the reaction temperature for the cyclization reaction ranges from −70° C. to 175° C., e.g., from −40° C. to 60° C. The pressure at which the reaction is conducted may vary widely. In one embodiment, the reaction is conducted at a pressure ranging from 0.01 MPa to 10 MPa, e.g., from 0.1 MPa to 5 MPa. Preferably, the reaction is conducted at atmospheric pressure.

The acetoacetamide salt may be introduced to the cyclization reactor and the cooled cyclizing agent composition, e.g., a solution of cyclizing agent optionally in solvent, may be metered into the reactor. In preferred embodiments, both reactants (acetoacetamide salt and cyclizing agent) are simultaneously fed into the reactor. In one embodiment, the cooled cyclizing agent composition is initially introduced into the reactor and the acetoacetamide salt is added. Preferably, at least part of the cyclizing agent composition is introduced into the reactor and, either continuously or in portions, acetoacetamide salt and (additional) cyclizing agent are then metered in, preferably while maintaining the temperature as described above.

The acetoacetamide salt may be introduced to the reactor and the cyclizing agent composition may be metered into the reactor. In preferred embodiments, both reactants are simultaneously fed into the reactor. In one embodiment, the cyclizing agent composition is initially introduced into the reactor and the acetoacetamide salt is added. Preferably, at least part of the cyclizing agent composition is introduced into the reactor and, either continuously or in portions, acetoacetamide salt and (additional) cyclizing agent are then metered in, preferably while maintaining the temperature as described above.

The formation of the crude acesulfame potassium composition from the cyclic sulfur trioxide adduct composition, in some embodiments, comprises the steps of hydrolyzing the cyclic sulfur trioxide adduct to form an acesulfame-H composition; neutralizing the acesulfame-H in the acesulfame H composition to form a crude acesulfame potassium composition; and forming the acesulfame potassium composition from the crude acesulfame potassium composition.

The cyclic sulfur trioxide adduct may be hydrolyzed via conventional means, e.g., using water. Thus, the forming step may comprise the steps of hydrolyzing the cyclic sulfur trioxide adduct to form an acesulfame-H composition. Acesulfame-H is referred to as sweetener acid.

An exemplary hydrolysis reaction scheme is shown in reaction (6), below.

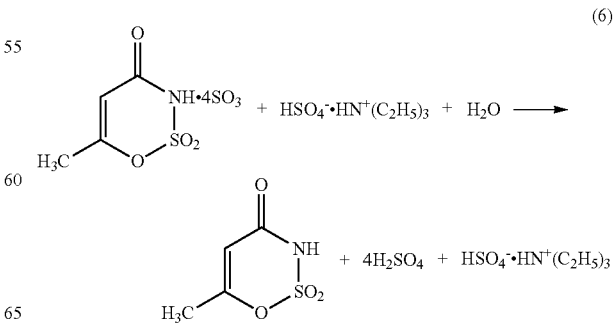

(6)

The addition of the water leads to a phase separation. The majority of the sweetener acid, acesulfame-H (6-methyl-3,4-dihydro-1,2,3-oxathiazin-4-one 2,2-dioxide), which is formed via the hydrolysis, is present in the organic phase, e.g., at least 60 wt %, at least 70%, at least 80%, or at least 90%. The remainder of the sweetener acid is in the water phase and can be extracted and optionally added to the sweetener acid in the organic phase. In cases where dichloromethane is used as the reaction medium, water or ice may be added, e.g., in a molar excess, based on the sulfur trioxide, to the cyclic sulfur trioxide adduct/sulfur trioxide solution.

In some cases, the hydrolysis step comprises adding water to the cyclic sulfur trioxide adduct. In preferred embodiments, the weight ratio of water to acetoacetamide salt is greater than 1.3:1, e.g., greater than 1.5:1, greater than 1.7:1, greater than 2:1 or greater than 2.2:1. Employment of these ratios may lead to decreases in acetoacetamide-N-sulfonic acid and/or acetoacetamide formation in the neutralized crude acesulfame potassium composition, e.g., the crude acesulfame potassium composition may comprise acetoacetamide-N-sulfonic acid in the amounts discussed herein.

It was surprisingly discovered that the temperature at which the water is initially fed to the hydrolysis reaction may have beneficial effects on impurity production, e.g., organic production or 5-chloro-acesulfame potassium production as well as reaction parameters, e.g., temperature. At lower temperatures, e.g., lower than approximately −35° C. or lower than −22° C., ice tends to build up in the reaction mixture. As this ice melted, it led to the onset of additional reaction, which caused the temperature to rise quickly. This rise in temperature surprisingly led to a product that contained much higher levels of impurities. In some cases, the hydrolyzing comprises adding hydrolysis water to the cyclic sulfur trioxide adduct to form a hydrolysis reaction mixture and reacting the mixture to from the acesulfame-H composition. In some embodiments, the temperature of the hydrolysis reaction mixture or the temperature at which the hydrolysis water is fed to the reactor is maintained at a temperature greater than −35° C., e.g., greater than −30° C., greater than −25° C., greater than −24° C., greater than −23° C., greater than −22° C., greater than −21.5° C., greater than −21° C., or greater than greater than −20° C. In terms of ranges, the temperature of the hydrolysis reaction mixture or the temperature at which the hydrolysis water is fed to the reactor optionally is maintained at a temperature ranging from −35° C. to 0° C., e.g., from −30° C. to −5° C., from −20° C. to −5° C., from −30° C. to −20° C., from −25° C. to −21° C., or −25° C. to −21.5° C.

After the addition of water, the reaction solvent, e.g., dichloromethane, may be removed by distillation, or the acesulfame-H that remains in the organic phase may be extracted with a more suitable solvent. Suitable solvents are those which are sufficiently stable towards sulfuric acid and which have a satisfactory dissolving capacity. Other suitable solvents include esters of carbonic acid such as, for example dimethyl carbonate, diethyl carbonate and ethylene carbonate, or esters of organic monocarboxylic acids such as, for example, isopropyl formate and isobutyl formate, ethyl acetate, isopropyl acetate, butyl acetate, isobutyl acetate and neopentyl acetate, or esters of dicarboxylic acids or amides which are immiscible with water, such as, for example, tetrabutylurea, are suitable. Isopropyl acetate and isobutyl acetate are particularly preferred.

It has now been discovered that a transition phase may form in addition to the organic sweetener acid-dichloromethane phase and aqueous phase. The transition phase may contain high amounts of impurities, e.g., acetoacetamide. The transition phase may contain higher amounts of such impurities than the organic phase. Beneficially, this transition phase may be removed from the organic sweetener acid-dichloromethane phase thus significantly reducing impurity content thereof. The process may utilize the step of phase separating the acesulfame-H composition. The phase separation may form the sweetener acid-dichloromethane phase, the aqueous phase, and the aforementioned transition phase comprising at least 2 wt % impurities, e.g., at least 5 wt %, at least 10 wt %, at least 20 wt %, at least 30 wt %, or at least 50 wt %. The process may comprise separating from the acesulfame-H composition the transition phase to form a purified acesulfame-H composition. The finished acesulfame potassium composition may then be formed from the purified acesulfame-H composition, e.g., via neutralization and treatment.

The combined organic phases are dried with, for example, $Na_2SO_4$, and are evaporated. Any sulfuric acid which has been carried over in the extraction may be removed by appropriate addition of aqueous alkali to the organic phase. For this purpose, dilute aqueous alkali may be added to the organic phase until the pH reached in the aqueous phase corresponds to that of pure 6-methyl-3,4-dihydro1,2,3-oxathiazin-4-one 2,2-dioxide at the same concentration in the same two-phase system of extracting agent and water.

Neutralization

The neutralization of the acesulfame-H yields a non-toxic salt of acesulfame-H, e.g., acesulfame potassium. In one embodiment, neutralization is carried out by reacting the acesulfame-H with an appropriate base, e.g., potassium hydroxide, in particular a membrane-produced potassium hydroxide. Other suitable bases include, for example, KOH, $KHCO_3$, $K_2CO_3$, and potassium alcoholates. An exemplary reaction scheme using potassium hydroxide as a neutralizing agent is shown in reaction (7), below.

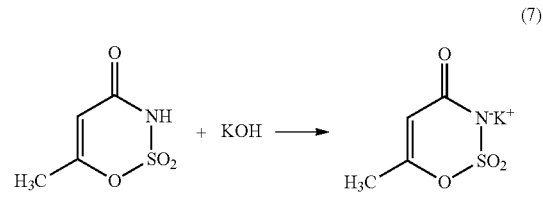

(7)

In some cases, the neutralization is conducted or maintained at a low pH levels, which may advantageously further result in a reduction or elimination of the formation of impurities, e.g., acetoacetamide salts. In this context, "conducted" means that the neutralization step begins at a low pH level, and "maintained" means that steps are taken to ensure that the pH stays within a low pH range throughout the entire neutralization step. In one embodiment, the neutralization step is conducted or maintained at a pH below 10.0, e.g., below 9.5, below 9.0, below 8.5, below 8.0, below 7.5, below 7.0, or below 6.5. In terms of ranges, the neutralization step is preferably conducted or maintained at a pH between 6.0 and 10.0, e.g., between 6.5 and 9.5, between 7.0 and 9.0, or between 7.5 and 8.5.

In some cases, the pH in the neutralizing step may be maintained within the desired range by managing the components of the neutralization reaction mixture, which comprises acesulfame-H and neutralizing agent (and also solvent). For example, the composition of the neutralization reaction mixture may include from 1 wt % to 95 wt % neutralizing agent, e.g., from 10 wt % to 85 wt % or from 25 wt % to 75 wt %, and from 1 wt % to 95 wt % acesulfame-H, e.g., from 10 wt % to 85 wt % or from 25 wt % to 75 wt %. These concentration ranges are based on the mixture of neutralization agent and acesulfame-H (not including solvent).

In one embodiment, the acesulfame-H may be neutralized and extracted directly from the purified organic extraction phase using an aqueous potassium base. The acesulfame potassium then precipitates out, where appropriate after evaporation of the solution, in the crystalline form, and it can also be recrystallized for purification.

In one embodiment, the process is not a small-scale batch process or a laboratory-scale process. For example, the inventive process for producing a finished acesulfame potassium composition may yield at least 50 grams of finished acesulfame potassium composition per batch, e.g., at least 100 grams per batch, at least 500 grams per batch, at least 1 kilogram per batch, or at least 10 kilograms per batch. In terms of rates, the inventive process may yield at least 50 grams of finished acesulfame potassium composition per hour, e.g., at least 100 grams per hour, at least 500 grams per hour, at least 1 kilogram per hour, or at least 10 kilograms per hour.

FIG. 1 shows an exemplary acesulfame potassium process 100 in accordance with the process described herein. Process 100 comprises amidosulfamic acid salt formation reactor 102 and acetoacetamide salt formation reactor 104. Although FIG. 1 shows separate reactors for the two intermediate formation reactions, other configurations, e.g., a one reactor process, are within the contemplation of the present process. Sulfamic acid is fed to amidosulfamic acid salt formation reactor 102 via sulfamic acid feed line 106. Amine(s), preferably triethylamine, are fed to amidosulfamic acid salt formation reactor 102 via amine feed line 108. In addition to sulfamic acid and amine(s), acetic acid is also fed to amidosulfamic acid salt formation reactor 102 (via feed line 110). The resultant reaction mixture in amidosulfamic acid salt formation reactor 102 is as discussed above. In amidosulfamic acid salt formation reactor 102, the sulfamic acid and the amine (in the presence of the acetic acid) are reacted to yield a crude amidosulfamic acid salt composition, which exits reactor 102 via line 112. Although not shown, a reaction solvent, e.g., dichloromethane may also be present in the amidosulfamic acid salt formation reactor 102.

The crude amidosulfamic acid salt composition in line 112 is directed to acetoacetamide salt formation reactor 104. Diketene is fed to acetoacetamide salt formation reactor 104 via feed line 114. In acetoacetamide salt formation reactor 104, the amidosulfamic acid salt and the diketene are reacted to yield a crude acetoacetamide salt composition, which exits reactor 104 via line 118. Although not shown, dichloromethane may also be present in the acetoacetamide salt formation reactor 104.

Cyclizing agent (sulfur dioxide) and solvent (dichloromethane) are fed to vessel 119 via feed lines 121 and 123. Vessel 119 is preferably a vessel wherein a cyclizing agent composition comprising these two components is formed. The cyclizing agent composition comprising both cyclizing agent and solvent exits vessel 119 via line 125.

The crude acetoacetamide salt composition is directed to cyclization reactor 120 via line 118. The cyclizing agent composition is also directed to cyclization reactor 120 (via line 125). Line 125 is preferably made of a material and in such a size and shape to facilitate the residence times discussed herein. In cyclization reactor 120, the acetoacetamide salt in the crude acetoacetamide salt composition in line 118 is cyclized and a cyclic sulfur trioxide adduct stream exits via line 124.

The cyclic sulfur trioxide adduct in line 124, is directed to hydrolysis reactor 126. Water is fed to hydrolysis reactor 126 via water feed 128. In hydrolysis reactor 126, the cyclic sulfur trioxide adduct is hydrolyzed to yield a crude acesulfame-H composition, which exits hydrolysis reactor 126 via line 130 and is directed to phase separation unit 132. Phase separation unit 132 separates the contents of line 130 into organic phase 134 and aqueous phase 136. Organic phase 134 comprises a major amount of the acesulfame-H in line 130 as well as solvent, e.g., methylene chloride. Aqueous phase 136 exits via line 137 and comprises triethylammonium sulfate, and optionally sulfuric acid and minor amounts of acesulfame-H. The aqueous phase may be further purified to separate and/or recover the acesulfame-H and/or the triethylammonium sulfate. The recovered acesulfame-H may be combined with the acesulfame from the organic phase (not shown).

Organic phase 134 exits phase separation unit 132 and is directed to extraction column 138 (via line 140). Water is fed to extraction column 138 via water feed 142. The water extracts residual sulfates from the contents of line 140 and a purified acesulfame-H composition exits extraction column 138 via line 144. The extracted sulfates exit extraction column 138 via line 145.

The purified acesulfame-H composition in line 144 is directed to neutralization unit 146. Potassium hydroxide is also fed to neutralization unit 146 (via line 148). The addition of the potassium hydroxide (via line 148) to neutralization unit 146 may be adjusted to achieve and/or maintain the desired pH levels during the neutralization, as discussed herein. The potassium hydroxide neutralizes the acesulfame-H in the purified acesulfame-H composition to yield a product comprising acesulfame potassium, dichloromethane, water, potassium hydroxide, and impurities, e.g., acetoacetamide, which exits neutralization unit 146 via line 150. This product may be considered a crude acesulfame potassium composition.

The crude acesulfame potassium product stream in line 150 may be directed to treatment zone 156 to recover finished acesulfame potassium, which is shown exiting via stream 152. In addition to the finished acesulfame potassium, dichloromethane and potassium hydroxide may be separated from the crude acesulfame potassium product stream, as shown by stream 154. The contents of stream 154 may be recovered and/or recycled to the process. Treatment zone 156 may comprise one or more of the treatment steps described herein, e.g., stripping, evaporation, crystallization, and filtration.

The product in line 150 is directed to phase separation unit 160. Phase separation unit 160 separates the product in line 150 into organic phase 162 and an aqueous phase 164. Aqueous phase 164 comprises a major amount of the acesulfame potassium in line 150 as well as some impurities. Organic phase 162 comprises potassium hydroxide, dichloromethane, and water and may be further treated to recover these components. Aqueous phase 164 (without any further treatment) may be considered a crude acesulfame potassium composition. Aqueous phase 164 may be optionally treated to form a finished acesulfame potassium composition.

Aqueous phase 164 is directed to treatment unit 156 via line 166. In treatment unit 156, aqueous phase 164 is treated to obtain finished acesulfame potassium composition (product that may be sold), which is shown exiting via stream 152. In addition to the finished acesulfame potassium composition, dichloromethane and potassium hydroxide may be separated. These components exit treatment unit 156 via line 154. The contents of stream 154 may be recovered and/or recycled to the process.

Figure 2:
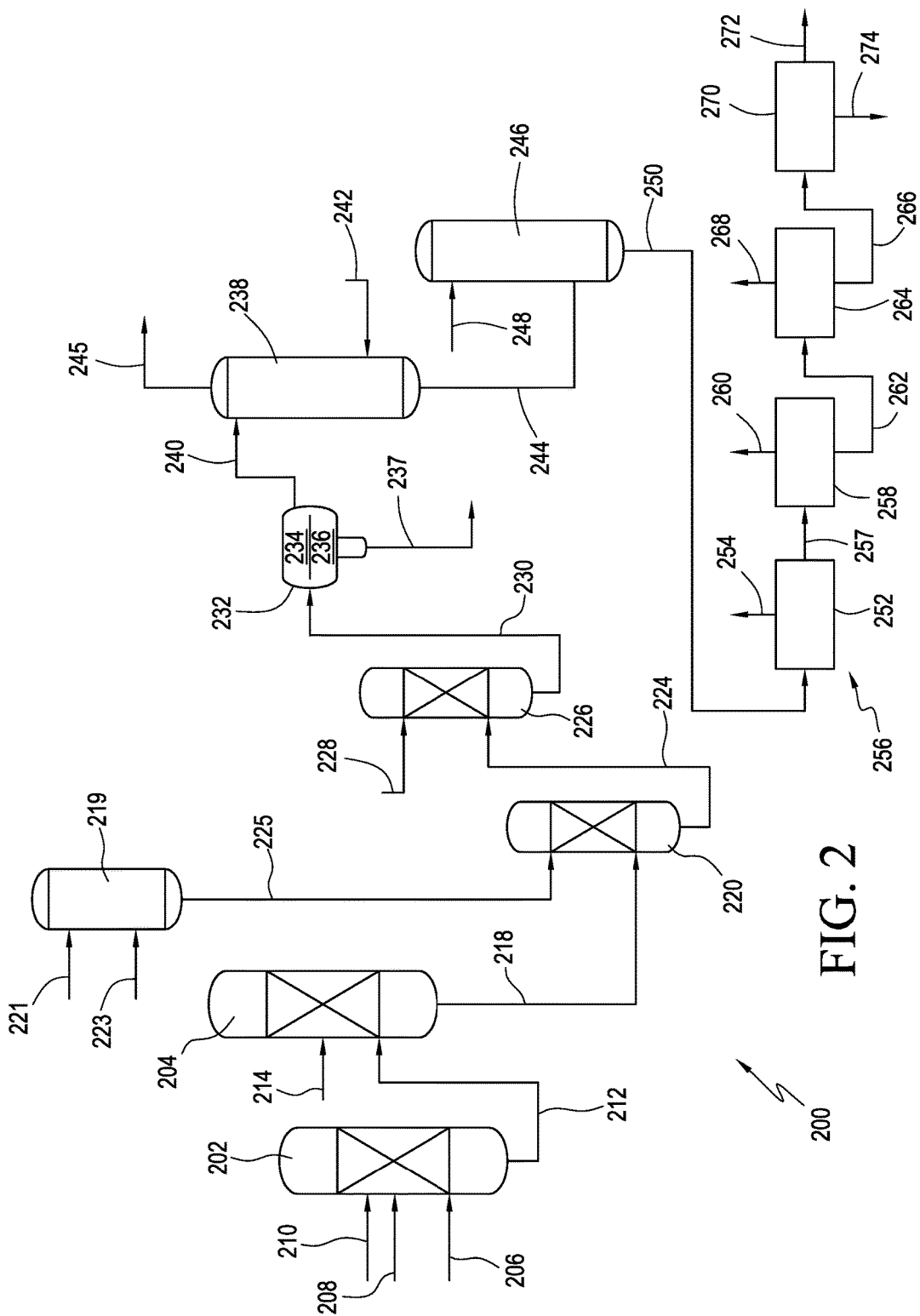
FIG. 2 is a process flow sheet of an acesulfame potassium production process employing one embodiment of a treatment scheme of the present invention.

FIG. 2 shows and exemplary treatment zone. Crude acesulfame potassium product stream 250 is fed to treatment zone 256. In particular, crude acesulfame potassium product stream 250 is fed to stripper 252 to strip solvent therefrom. Solvent in stream 254 exits stripper 252 and is directed to further processing, e.g. re-use or recycling. Stripped acesulfame potassium stream 257 comprises low amounts of solvent and exits stripper 252 and is directed to evaporator 258. It has been found that the removal of solvent prior to evaporation unexpectedly provides the benefit of improved evaporation operations.

Evaporator 258 removes water from stripped acesulfame potassium stream in line 257 to form water stream 260 and intermediate acesulfame potassium composition stream 262. Evaporator 258 is preferably a falling film evaporator. Intermediate acesulfame potassium composition stream 262 is directed to crystallizer 264, which yields crystal-containing stream 266 and recycle stream 268. Crystal-containing stream 266 is then directed to filtration unit 270, which filters impurities to yield finished acesulfame potassium composition stream 272 and impurity stream 274. The treatment units may beneficially be operated at the separation parameters discussed herein.

The invention relates also to the following aspects:

Aspect 1: A process for producing a finished acesulfame potassium composition, the process comprising the steps of:
(a) providing a crude acesulfame potassium composition comprising acesulfame potassium, acetoacetamide and water;
(b) concentrating the crude acesulfame potassium composition to form a water stream and an intermediate acesulfame potassium composition comprising acesulfame potassium and less than 33 wppm acetoacetamide; and
(c) separating the intermediate acesulfame potassium composition to form the finished acesulfame potassium composition comprising acesulfame potassium and less than 33 wppm acetoacetamide;
wherein the concentrating step (b) is conducted at a temperature below 90° C., and wherein the separating step (c) is conducted at a temperature at or below 35° C.

Aspect 2: The process of aspect 1, wherein the providing step (a) comprises:
reacting sulfamic acid and an amine to form an amidosulfamic acid salt;
reacting the amidosulfamic acid salt and acetoacetylating agent to form an acetoacetamide salt;
reacting the acetoacetamide salt with cyclizing agent in the cyclizing agent composition to form the cyclic sulfur trioxide adduct;
hydrolyzing the cyclic sulfur trioxide adduct to form an acesulfame-H composition comprising acesulfame-H; and
neutralizing the acesulfame-H in the acesulfame-H composition to form the crude acesulfame potassium composition.

Aspect 3: The process of any one of the preceding aspects, wherein the intermediate acesulfame potassium composition comprises less than 33 wppm acetoacetamide-N-sulfonic acid.

Aspect 4: The process of any one of the preceding aspects, wherein the concentrating comprises: evaporating the crude acesulfame potassium composition to form the water stream and the intermediate acesulfame potassium composition comprising acesulfame potassium and less than 75 wt % water.

Aspect 5: The process of any one of the preceding aspects, wherein evaporation residence time is less than 180 minutes.

Aspect 6: The process of any one of the preceding aspects, wherein the intermediate acesulfame potassium composition comprises less than 33 wppm acetoacetamide-N-sulfonic acid.

Aspect 7: The process of any one of the preceding aspects, wherein the separating comprises:
crystallizing the intermediate acesulfame potassium composition to form acesulfame potassium crystals; and
filtering the acesulfame potassium crystals to form the finished acesulfame potassium composition.

Aspect 8: The process of any one of the preceding aspects, wherein the filtering is conducted at a temperature at or below 35° C.

Aspect 9: The process of any one of the preceding aspects, wherein the crystallizing is conducted at a temperature at or below 35° C.

Aspect 10: The process of any one of the preceding aspects, wherein the crystallizing is conducted at a pH below 10.

Aspect 11: The process of any one of the preceding aspects, wherein the evaporating is conducted at a temperature below 85° C. and the intermediate acesulfame potassium composition comprises from 1 wppb to 33 wppm acetoacetamide and the finished acesulfame potassium composition comprises less than 33 wppm acetoacetamide.

Aspect 12: The process of any one of the preceding aspects, wherein the intermediate acesulfame potassium composition further comprises less than 33 wppm acetoacetamide-N-sulfonic acid.

Aspect 13: The process of any one of the preceding aspects, wherein the evaporating is conducted at a temperature below 60° C. and the evaporator residence time is less than 50 minutes and the intermediate acesulfame potassium composition comprises from 10 wppb to 25 wppm acetoacetamide and the finished acesulfame potassium composition comprises from 10 wppb to 15 wppm acetoacetamide.

Aspect 14: The process of any one of the preceding aspects, wherein the intermediate acesulfame potassium composition comprises less than 30 wppm acetoacetamide-N-sulfonic acid.

Aspect 15: The process of any one of the preceding aspects, wherein the evaporating is conducted at a temperature ranging from 20° C. to 55° C.; the evaporator residence time ranges from 1 minute to 300 minutes; the separating is conducted at a temperature ranging from −10° C. to 15° C.; the separating operation residence time ranges from 1 to 180 minutes; the crude acesulfame potassium composition comprises from 500 wppm to 2375 wppm acetoacetamide; the intermediate acesulfame potassium composition comprises 10 wppb to 20 wppm acetoacetamide and 10 wppb to 20 wppm acetoacetamide-N-sulfonic acid; and the finished acesulfame potassium composition comprises from 10 wppb to 10 wppm acetoacetamide, and from 1 wppb to 20 wppm acetoacetamide-N-sulfonic acid.

Aspect 16: The process of any one of the preceding aspects, wherein:
(i) the evaporating is conducted at a temperature below 46° C.,
(ii) the evaporator residence time is less than 30 minutes,
(iii) crystallizing is conducted at a temperature below 35° C., (iv) the intermediate acesulfame potassium composition comprises from 10 wppb to 12 wppm acetoacetamide, and (v) the finished acesulfame potassium composition comprises from 10 wppb to 7 wppm acetoacetamide.

Aspect 17: The process of any one of the preceding aspects, wherein the intermediate acesulfame potassium composition comprises less than 20 wppm acetoacetamide-N-sulfonic acid.

Aspect 18: The process of any one of the preceding aspects, wherein the crude acesulfame composition further comprises solvent and wherein the process further comprises removing solvent from the crude acesulfame potassium composition prior to the evaporation.

Aspect 19: The process of any one of the preceding aspects, wherein the weight percentage of acetoacetamide in the finished acesulfame potassium composition is less than the weight percentage of acetoacetamide in the crude acesulfame potassium composition.

Aspect 20: The process of any one of the preceding aspects, further comprising:

separating from the acesulfame-H composition a transition phase comprising at least 2 wt % acetoacetamide to form a purified acesulfame-H composition.

Aspect 21: The process of any one of the preceding aspects, wherein the neutralizing comprises neutralizing the acesulfame-H in the purified acesulfame-H composition to form the crude acesulfame potassium composition comprising acesulfame potassium and acetoacetamide.

Aspect 22: The process of any one of the preceding aspects, wherein the concentrating comprises evaporating the crude acesulfame potassium composition to form a water stream and an intermediate acesulfame potassium composition comprising acesulfame potassium and less than 50 wt % water, and the separating comprises crystallizing the intermediate acesulfame potassium composition to form a crystal-containing stream comprising acesulfame potassium crystals, and filtering the crystal-containing stream to form the finished acesulfame potassium composition.

Aspect 23: The process of any one of the preceding aspects, wherein the filtering comprises at least two filtration operations.

Aspect 24: A finished acesulfame potassium composition produced or producible by, or obtainable or obtained from the process of any one of aspects 1 to 22.

Aspect 25: A process for producing a finished acesulfame potassium composition, the process comprising the steps of:
(a) reacting sulfamic acid and triethylamine to form an amidosulfamic acid salt;
(b) reacting the amidosulfamic acid salt and diketene to form acetoacetamide salt;
(c) contacting dichloromethane and a sulfur trioxide to form a cyclizing agent composition; (d) reacting the acetoacetamide salt with sulfur trioxide in the cyclizing agent composition to form a cyclic sulfur trioxide adduct;
(e) hydrolyzing the cyclic sulfur trioxide adduct to form an acesulfame-H composition;
(f) neutralizing the acesulfame-H to form the crude acesulfame potassium composition comprising acesulfame potassium and acetoacetamide,
(g) evaporating the crude acesulfame potassium composition to form a water stream and an intermediate acesulfame potassium composition comprising acesulfame potassium and less than 75 wt % water;
(h) crystallizing the intermediate acesulfame potassium composition to form acesulfame potassium crystals; and (i) filtering the acesulfame potassium crystals to form the finished acesulfame potassium composition comprising acesulfame potassium and less than 10 wppm acetoacetamide, wherein the evaporating is conducted at a temperature below 50° C. and wherein evaporator residence time is less than 30 minutes.

Aspect 26: The process of aspect 25, wherein filtering is conducted at a temperature below 35° C. and crystallizing is conducted at a temperature below 35° C.

Aspect 27: A finished acesulfame potassium composition produced or producible by, or obtainable or obtained from the process of aspects 25 or 25.

Aspect 28: An acesulfame potassium composition comprising acesulfame potassium and less than 33 wppm, preferably less than 10 wppm acetoacetamide.

Aspect 29: The acesulfame potassium composition of aspect 27 or 28, further comprising less than 33 wppm, preferably less than 10 wppm acetoacetamide-N-sulfonic acid.

Aspect 30: The acesulfame potassium composition of aspect 27-29, further comprising 0.001 wppm to 5 wppm organic impurities and/or 0.001 wppm to 5 wppm of at least one heavy metal.

Aspect 31: The acesulfame potassium composition of aspect 27-30, wherein the at least one heavy metal is selected from the group consisting of mercury, lead and mixtures thereof.

Aspect 31: The acesulfame potassium composition of aspect 27-31, wherein the mercury is present in an amount of 1 wppb to 20 wppm.

Aspect 31: The acesulfame potassium composition of aspect 27-32, wherein the lead is present in an amount of 1 wppb to 25 wppm.

EXAMPLES

The following examples are included to illustrate the process and compositions and are not meant to limit the scope of the application.

Crude Acesulfame Potassium Composition Formation 100 mmol of 99.5% pure sulfamic acid was suspended in 50 mL dichloromethane in a flask with reflux. Under continuous agitation, 105 mmol of trimethylamine was added within approximately 3 minutes. During this time, temperature increased due to acid/base exothermal reaction up to about 42° C. (the boiling point of dichloromethane). This first reaction mixture was stirred for approximately 15 additional minutes, until no solid sedimentation was seen in the flask. Then, 10 mmol of acetic acid was added to the first reaction mixture and was stirred for approximately 15 additional minutes. At this point, within 7 minutes of the addition of the acetic acid, 110 mmol of diketene was added dropwise to form a second reaction mixture. After the addition of all of the diketene was added to the second reaction mixture and approximately 15 minutes of reaction time, this second reaction mixture was cooled. The resultant cooled second reaction mixture contained approximately 30% acetoacetamide N-sulfonate triethylammonium salt. Additional batches of cooled second reaction mixture were prepared as necessary.

In a separate vessel, a sulfur trioxide/dichloromethane composition comprising approximately 15 wt % sulfur trioxide and approximately 85 wt % dichloromethane was prepared by contacting the two components with one another.

A second flask (a 4 necked round bottom flask equipped with mechanical stirrer, thermometer, and feed vessels) was placed into a cooling bath containing a mixture of isopropanol and dry ice. Approximately 200 g of the acetoacetamide-N-sulfonate triethylammonium salt solution and approximately 577 g of the sulfur trioxide/dichloromethane compositions were measured. Approximately 15 wt % of the total sulfur trioxide/dichloromethane composition (approximately 87 g) was initially fed to the reaction flask under continuous agitation by mechanical stirrer. When the temperature of the flask contents reached −35° C. (due to the cooling bath), the remainder of the sulfur trioxide/dichloromethane composition and all of the acetoacetamide-N-sulfonate triethylammonium salt solution were fed into the second flask. The time period that the solvent contacts the cyclizing agent before formation of the cyclic sulfur trioxide adduct, e.g., before the acetoacetamide-N-sulfonate triethylammonium salt solution was fed to the second flask, was less than an hour. The feed rate was controlled in such a way that the temperature of the second flask contents remained between −25° and −35° C. during the feeding/cyclization reaction. After the reactants were fed, the reaction was allowed to proceed for approximately one additional minute. The cooling bath was then removed.

After approximately one minute, the temperature of the flask contents reached approximately −22° C. At this time, hydrolysis was initiated by feeding deionized water to the flask. Water was fed over 10 minutes. The hydrolysis reaction was exothermic. Water was added slowly so as to maintain temperature between −20° C. and −5° C. After addition of water, reaction mixture was allowed to reach room temperature.

The hydrolyzed product was phase separated via a separating funnel. A heavier organic sweetener acid-dichloromethane phase (acesulfame-H composition) was separated out, and the remaining aqueous phase was discarded.

The acesulfame-H in the acesulfame-H composition was neutralized with a 10% potassium hydroxide solution. Neutralization was carried out at 25° C.±1° C. Potassium hydroxide addition was completed within 20 minutes. After completion of the neutralization step, an additional phase separation was performed using a separating funnel to yield an aqueous phase containing acesulfame potassium (and some impurities) and an organic phase. The aqueous phase was considered a crude acesulfame potassium composition. This crude acesulfame potassium composition was split into two portions and treated as discussed below. The remaining dichloromethane in the organic phase was discarded.

Example 1: Evaporation/Crystallization

A first portion of the crude acesulfame potassium composition was evaporated in a rotary evaporator at 45° C. and under reduced pressure for approximately 20 minutes. As a result, approximately 50% of the water was evaporated from the crude acesulfame potassium composition. After the water was removed an intermediate acesulfame potassium composition remained. The intermediate acesulfame potassium composition was then separated, e.g., cooled to 5° C. in a refrigerator.

The cooling resulted in the precipitation of crude crystals containing mostly acesulfame potassium. These crude crystals were considered a finished acesulfame potassium composition. The crude crystals were separated from the liquid and analyzed for yield and impurities, e.g., acetoacetamide. Testing for acetoacetamide (AAA) content was performed using the HPLC equipment and techniques discussed herein. In particular, the HPLC analysis was performed using an LC Systems HPLC unit from Shimadzu having a CBM-20 Shimadzu controller and being equipped with an IonPac NS1 ((5 μm) 150×4 mm) analytical column and an IonPac NG1 guard column (35×4.0 mm). A Shimadzu SPD-M20A photodiode array detector was used for detection (at 270 nm and 280 nm wavelength). Analysis was performed at 23° C. column temperature. As a first eluent solution, an aqueous mixture of tetra butyl ammonium hydrogen sulfate (3.4 g/L), acetonitrile (300 mL/L), and potassium hydroxide (0.89 g/L) was employed; as a second eluent solution, an aqueous mixture of tetra butyl ammonium hydrogen sulfate (3.4 g/L) and potassium hydroxide (0.89 g/L) was employed. Elution was conducted in gradient mode according to the following second eluent flow profile:

0 to 3 minutes: constant 80% (v/v)
3 to 6 minutes: linear reduction to 50% (v/v)
6 to 15 minutes: constant at 50% (v/v)
15 to 18 minutes: linear reduction to 0%
18 to 22 minutes: constant at 0%
22 to 24 minutes: linear increase to 80% (v/v)
24 to 35 minutes constant at 80% (v/v).

Overall flow rate of eluent was approximately 1.2 mL/min. The data collection and calculations were performed using Lab Solution software from Shimadzu.

Comparative Example A: Evaporation/Crystallization

A second portion of the crude acesulfame potassium composition was evaporated in a rotary evaporator at 90° C. and under reduced pressure for approximately 180 minutes. As a result, approximately 50% of the water was evaporated from the crude acesulfame potassium composition. After the water was removed an intermediate acesulfame potassium composition remained. The intermediate acesulfame potassium composition was then separated, e.g., cooled to 5° C. in a refrigerator.

The cooling resulted in the precipitation of crude crystals containing mostly acesulfame potassium. These crude crystals were considered a finished acesulfame potassium composition. The crude crystals were separated from the liquid and analyzed for yield and impurities, e.g., acetoacetamide. Testing for acetoacetamide content was performed using the HPLC equipment and techniques discussed above. The results for Example 1 and Comparative Example A are shown in Table 1.

TABLE 1

| | ACK Impurity Testing Immediately After First Evaporation/Crystallization | | | |
|---|---|---|---|---|
| | Evap. Temp., ° C. | Evap. Time, min. | Crystallization Temp., ° C. | AAA, wppm, in the finished ACK composition |
| Example 1 | 45° C. | 20 min. | 5° C. | 5 wppm |
| Comp. Ex. A | 90° C. | 180 min. | 5° C. | 37 wppm |

The temperature of the concentrating of the crude acesulfame potassium composition and the separating operation of the intermediate acesulfame potassium composition have an influence on acetoacetamide formation. Without being bound by theory, it is believed that acetoacetamide impurities form as a result of thermal stress during high temperature concentration of the crude acesulfame potassium composition, e.g., during the initial evaporation step. As shown, if the temperature of the concentrating operation is kept below 90° C., then additional post-crystallization separation is not needed to keep acetoacetamide content below a suitable level, e.g., less than 10 wppm.

Examples 2 and Comparative Examples B-D

The degradation effects of temperature and pH on acesulfame potassium compositions during treatment were also explored. Acesulfame potassium was diluted in sufficient water to form a 16% aqueous solution. The aqueous solution was divided into multiple portions (Example 2 and Comparative Examples B-D). These portions of aqueous solution (except for Example 2) were heated under reflux condensing to simulate the concentrating operation. In Comparative Example D, prior to heating, a small amount of 10% potassium hydroxide was added to the respective portion of aqueous solution, which brought the pH of the resultant solution to approximately 9.8. For each portion, crystals (intermediate acesulfame potassium compositions) were removed from the remaining liquid (after heating) and analyzed for and impurities formed via degradation, e.g., acetoacetamide-N-sulfonic acid (AAA-NSH). Testing for acetoacetamide-N-sulfonic acid content was performed using the HPLC equipment and techniques discussed above. The treatment conditions and resultant impurity contents are shown in Table 2.

TABLE 2

Effects of Temperature and pH on Degradation Products

| | Temp., ° C. | Heating Time, min. | pH | AAA-NSH, wppm, in the int. acesulfame potassium composition |
|---|---|---|---|---|
| Example 2 | 25° C. | — | 6.5 | 19 wppm |
| Comp. Ex. B | 95° C. | 180 min. | 6.5 | 33 wppm |
| Comp. Ex. C | 95° C. | 360 min. | 6.5 | 41 wppm |
| Comp. Ex. C | 95° C. | 180 min. | 9.8 | 89 wppm |

As shown in Table 2, the use of high temperature, heating time (which simulates residence time), and pH during conventional concentrating operation conditions results in degradation of acesulfame potassium (or acesulfame-H), which leads to the formation of additional impurities, e.g., acetoacetamide-N-sulfonic acid. By utilizing the concentrating operation parameters discussed herein, impurities formed via degradation are reduced or eliminated, which leads to higher purity finished acesulfame potassium compositions, i.e., finished acesulfame potassium compositions with low acetoacetamide-N-sulfonic acid content.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing a finished acesulfame potassium composition, the process comprising the steps of:
   (a) providing a crude acesulfame potassium composition comprising acesulfame potassium, acetoacetamide and water;
   (b) concentrating the crude acesulfame potassium composition to form a water stream and an intermediate acesulfame potassium composition; and
   (c) separating the intermediate acesulfame potassium composition to form the finished acesulfame potassium composition comprising acesulfame potassium and less than 33 wppm acetoacetamide;
   wherein the concentrating step (b) is conducted at a temperature below 90° C., and wherein the separating step (c) is conducted at a temperature at or below 35° C.

2. The process of claim 1, wherein the providing step (a) comprises:
   reacting sulfamic acid and an amine to form an amidosulfamic acid salt;
   reacting the amidosulfamic acid salt and acetoacetylating agent to form an acetoacetamide salt;
   reacting the acetoacetamide salt with cyclizing agent in the cyclizing agent composition to form the cyclic sulfur trioxide adduct;
   hydrolyzing the cyclic sulfur trioxide adduct to form an acesulfame-H composition comprising acesulfame-H; and
   neutralizing the acesulfame-H in the acesulfame-H composition to form the crude acesulfame potassium composition.

3. The process of claim 1, wherein the intermediate acesulfame potassium composition comprises less than 33 wppm acetoacetamide and less than 33 wppm acetoacetamide-N-sulfonic acid.

4. The process of claim 1, wherein the concentrating comprises: evaporating the crude acesulfame potassium composition to form the water stream and the intermediate acesulfame potassium composition comprising acesulfame potassium and less than 75 wt % water.

5. The process of claim 4, wherein evaporation residence time is less than 180 minutes.

6. The process of claim 5, wherein the intermediate acesulfame potassium composition comprises less than 33 wppm acetoacetamide-N-sulfonic acid.

7. The process of claim 4, wherein the separating comprises:
   crystallizing the intermediate acesulfame potassium composition to form acesulfame potassium crystals; and
   filtering the acesulfame potassium crystals to form the finished acesulfame potassium composition.

8. The process of claim 7, wherein the filtering is conducted at a temperature at or below 35° C.

9. The process of claim 7, wherein the crystallizing is conducted at a temperature at or below 35° C.

10. The process of claim 7, wherein the crystallizing is conducted at a pH below 10.

11. The process of claim 4, wherein the evaporating is conducted at a temperature below 85° C. and the finished acesulfame potassium composition comprises less than 33 wppm acetoacetamide.

12. The process of claim 11, wherein the intermediate acesulfame potassium composition comprises from 1 wppb to 33 wppm acetoacetamide and less than 33 wppm acetoacetamide-N-sulfonic acid.

13. The process of claim 4, wherein the evaporating is conducted at a temperature below 60° C. and the evaporator residence time is less than 50 minutes and the finished acesulfame potassium composition comprises from 10 wppb to 15 wppm acetoacetamide.

14. The process of claim 13, wherein the intermediate acesulfame potassium composition comprises from 10 wppb to 25 wppm acetoacetamide and less than 30 wppm acetoacetamide-N-sulfonic acid.

15. The process of claim 4, wherein the evaporating is conducted at a temperature ranging from 20° C. to 55° C., the evaporator residence time ranges from 1 minute to 300 minutes, the separating is conducted at a temperature ranging from −10° C. to 15° C., the separating operation residence time ranges from 1 to 180 minutes, the finished acesulfame potassium composition comprises from 10 wppb to 10 wppm acetoacetamide, and from 1 wppb to 20 wppm acetoacetamide-N-sulfonic acid.

16. The process of claim 4, wherein:
(i) the evaporating is conducted at a temperature below 46° C.,
(ii) the evaporator residence time is less than 30 minutes,
(iii) crystallizing is conducted at a temperature below 35° C.,
and
(iv) the finished acesulfame potassium composition comprises from 10 wppb to 7 wppm acetoacetamide.

17. The process of claim 16, wherein the intermediate acesulfame potassium composition comprises from 10 wppb to 12 wppm acetoacetamide and less than 20 wppm acetoacetamide-N-sulfonic acid.

18. The process of claim 4, wherein the crude acesulfame composition further comprises solvent and wherein the process further comprises removing solvent from the crude acesulfame potassium composition prior to the evaporation.

19. The process of claim 4, wherein the weight percentage of acetoacetamide in the finished acesulfame potassium composition is less than the weight percentage of acetoacetamide in the crude acesulfame potassium composition.

20. The process of claim 2, further comprising:
separating from the acesulfame-H composition a transition phase comprising at least 2 wt % acetoacetamide to form a purified acesulfame-H composition.

21. The process of claim 20, wherein the neutralizing comprises neutralizing the acesulfame-H in the purified acesulfame-H composition to form the crude acesulfame potassium composition.

22. The process of claim 1, wherein the concentrating comprises evaporating the crude acesulfame potassium composition to form a water stream and an intermediate acesulfame potassium composition comprising acesulfame potassium and less than 50 wt % water, and the separating comprises crystallizing the intermediate acesulfame potassium composition to form a crystal-containing stream comprising acesulfame potassium crystals, and filtering the crystal-containing stream to form the finished acesulfame potassium composition.

23. The process of claim 22, wherein the filtering comprises at least two filtration operations.

24. The process of claim 2, wherein the crude acesulfame potassium composition is evaporated to form the water stream and the intermediate acesulfame potassium composition.

25. The process of claim 24, wherein the intermediate acesulfame potassium composition comprises less than 75 wt % water.

26. The process of claim 24, wherein the crude acesulfame potassium composition is evaporated at a temperature of less than 50° C. and the evaporator residence time is less than 30 minutes.

27. The process of claim 24, wherein the intermediate acesulfame potassium composition is crystallized to form acesulfame crystals.

28. The process of claim 27, wherein the intermediate acesulfame potassium composition is crystallized at a temperature of below 35° C.

29. The process of claim 27, wherein acesulfame crystals are filtered to form the finished acesulfame composition.

30. The process of claim 27, wherein acesulfame crystals are filtered at a temperature below 35° C.

31. The process of claim 1, wherein the finished acesulfame potassium composition comprises from 10 wppb to 15 wppm acetoacetamide.

32. The process of claim 1, wherein the finished acesulfame potassium composition comprises from 10 wppb to 10 wppm acetoacetamide.

33. The process of claim 1, wherein the finished acesulfame potassium composition comprises from 10 wppb to 7 wppm acetoacetamide.

34. The process of claim 1, wherein the finished acesulfame potassium composition comprises less than 33 wppm acetoacetamide-N-sulfonic acid.

35. The process of claim 1, wherein the finished acesulfame potassium composition comprises from 1 wppb to 20 wppm acetoacetamide-N-sulfonic acid.

36. The process of claim 1, wherein the finished acesulfame potassium composition comprises from 10 wppb to 10 wppm acetoacetamide and from 1 wppb to 20 wppm acetoacetamide-N-sulfonic acid.

37. The process of claim 1, wherein the finished acesulfame potassium composition comprises 0.001 wppm to 5 wppm organic impurities and/or 0.001 wppm to 5 wppm of at least one heavy metal.

* * * * *